United States Patent
Luckhart et al.

(10) Patent No.: US 10,154,974 B1
(45) Date of Patent: Dec. 18, 2018

(54) USE OF ABSCISIC ACID FOR THE PREVENTION AND TREATMENT OF MALARIA

(71) Applicant: The Regents of the University of California, Oakland, CA (US)

(72) Inventors: Shirley Luckhart, Davis, CA (US); Elizabeth K. K. Glennon, Santa Monica, CA (US)

(73) Assignee: The Regents Of The University Of California, Oakland, CA (US)

( * ) Notice: Subject to any disclaimer, the term of this patent is extended or adjusted under 35 U.S.C. 154(b) by 0 days.

(21) Appl. No.: 15/294,630

(22) Filed: Oct. 14, 2016

Related U.S. Application Data

(60) Provisional application No. 62/242,587, filed on Oct. 16, 2015.

(51) Int. Cl.
*A61K 31/19* (2006.01)
*A61K 9/00* (2006.01)

(52) U.S. Cl.
CPC .......... *A61K 31/19* (2013.01); *A61K 9/0053* (2013.01)

(58) Field of Classification Search
CPC ................ A61K 31/19; A61K 9/0053
See application file for complete search history.

(56) References Cited

U.S. PATENT DOCUMENTS

| | | | |
|---|---|---|---|
| 7,741,367 | B2 | 6/2010 | Bassaganya-Riera et al. |
| 8,367,727 | B2 * | 2/2013 | Bassaganya-Riera ........ A61K 31/19 514/557 |
| 8,617,575 | B2 | 12/2013 | Ito et al. |
| 8,993,624 | B2 | 3/2015 | Bassaganya-Riera et al. |

FOREIGN PATENT DOCUMENTS

CN 102273455 B 2/2014

OTHER PUBLICATIONS

Delves et al (PLoS Medicine, 2012, 9(2), e1001169, 1-13).*
Glennon et al (Keystone Symposia, Poster Presentation, May 12-17, 2015, abstract).*
Boggild (Clinical Infectious Diseases, 2009, 49, 841-849).*
Serghides (hereinafter, "Serghides", PPAR Research, 2012, 1-12).*
Glennon (Year: 2015).*
Glennon et al., "Abscisic Acid: A Supplement to Reduce Plasmodium Disease Severity and Transmission", Abstract of poster presentation made at the Keystone Symposia entitled "The Arthropod Vector: The Controller of Transmission" held in Taos, New Mexico, May 12-17, 2015, 1 page.
Glennon et al., "Supplementation with Abscisic Acid Reduces Malaria Disease Severity and Parasite Transmission", American Journal of Tropical Medicine and Hygiene, vol. 94, No. 6, 2016, pp. 1266-1275.
Travassos et al., "Antimalarial drugs: An overview", UpToDate, Retrieved from <https://www.uptodate.com/contents/antimalarial-drugs-an-overview>, Sep. 10, 2015, 15 pages.
Avandia [rosiglitazone maleate] (1999, Revised 2016). Package insert. GlaxoSmithKline, Research Triangle Park, NC, 45 pages.
Glennon et al., "Abscisic acid induces a transient shift in signaling that enhances NK-κB-mediated parasite killing in the midgut of Anopheles stephensi without reducing lifespan or fecundity," Parasites & Vectors, 10:333, 2017, 12 pages.
Glennon et al., "Elevated plasma abscisic acid is associated with asymptomatic falciparum malaria and with IgG-/caspase-1-dependent immunity in Plasmodium yoelii-infected mice," Scientific Reports, 8:8896, 2018, 13 pages.
Serghides et al., "Rosiglitazone modulates the innate immune response to Plasmodium falciparum infection and improves outcome in experimental cerebral malaria," J Infect Dis, 199:1536-1545, 2009.

* cited by examiner

*Primary Examiner* — Rachael E Bredefeld
*Assistant Examiner* — Ibrahim D Bori
(74) *Attorney, Agent, or Firm* — Morrison & Foerster LLP

(57) ABSTRACT

The present disclosure provides methods for treating or preventing malaria by administration of abscisic acid, analogs or pharmaceutical salts thereof to a mammalian subject infected with or at risk of exposure to *Plasmodium*. In some aspects, the therapeutic and prophylactic regimens of the present disclosure are effective in reducing parasitemia and gametocytemia in a mammalian subject and/or reducing transmission of *Plasmodium* by a mosquito vector.

17 Claims, 30 Drawing Sheets

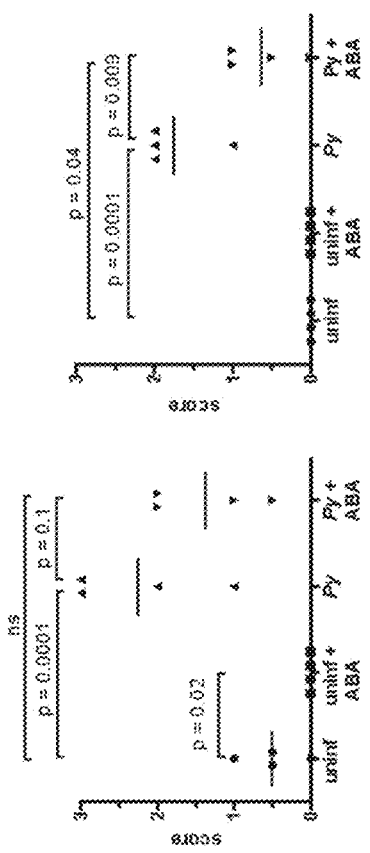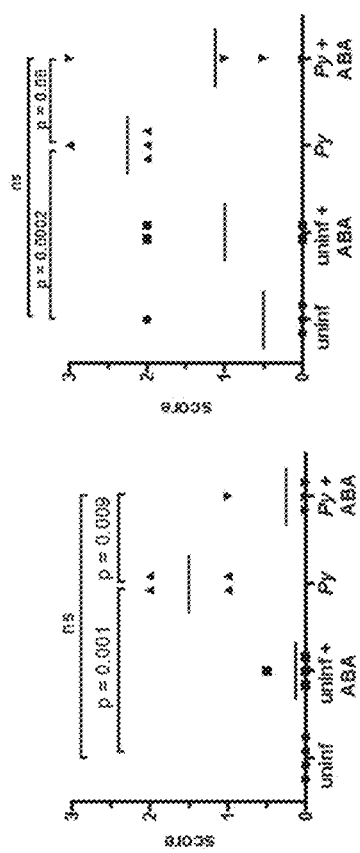
FIG. 3A leukocytes  FIG. 3B adherent leukocytes
FIG. 3C microabcesses  FIG. 3D hyperplasia

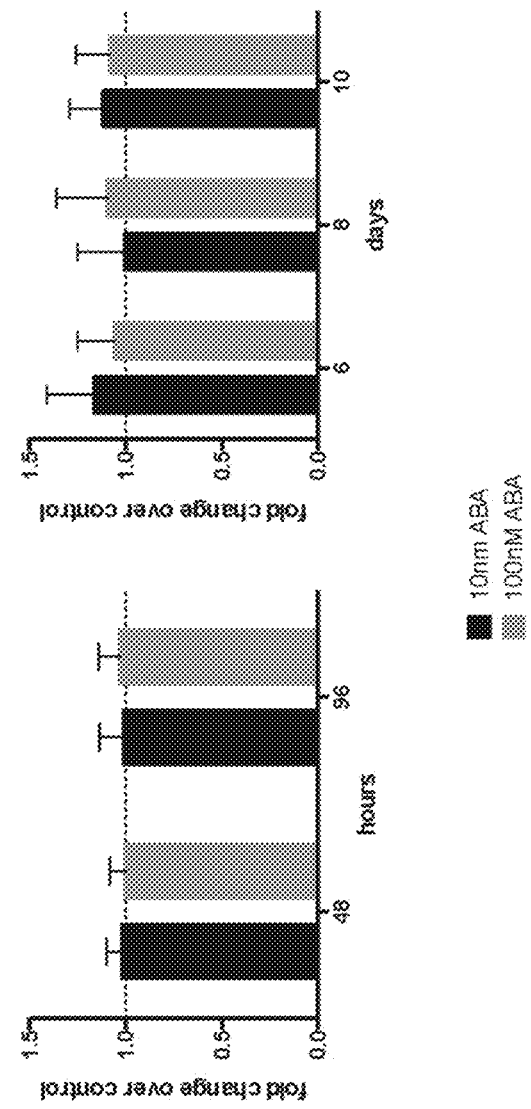
FIG. 7A asexual parasites    FIG. 7B gametocytes

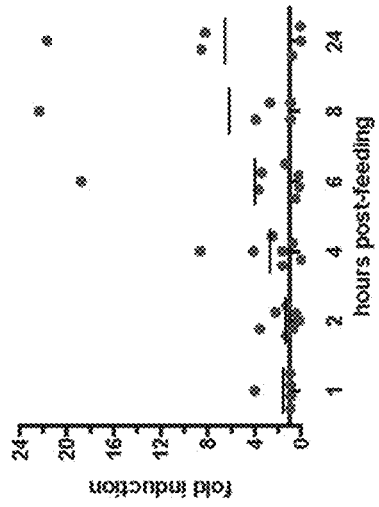
FIG. 9A Defensin
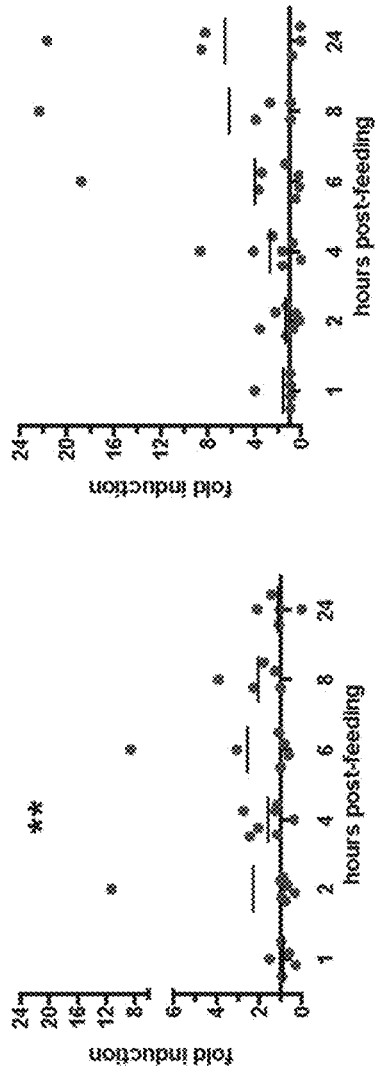
FIG. 9B LRIM
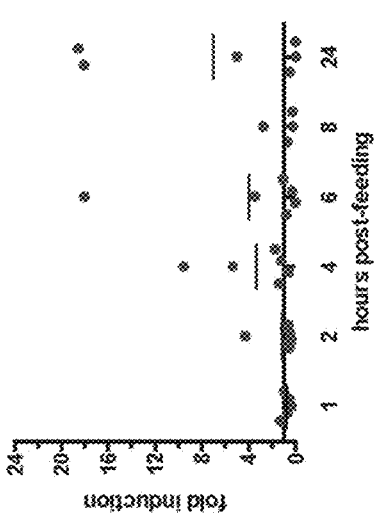
FIG. 9C APL1
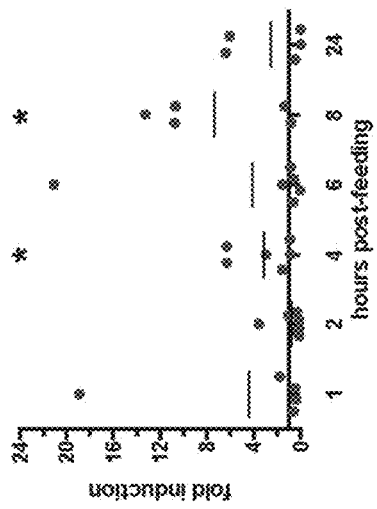
FIG. 9D TEP1

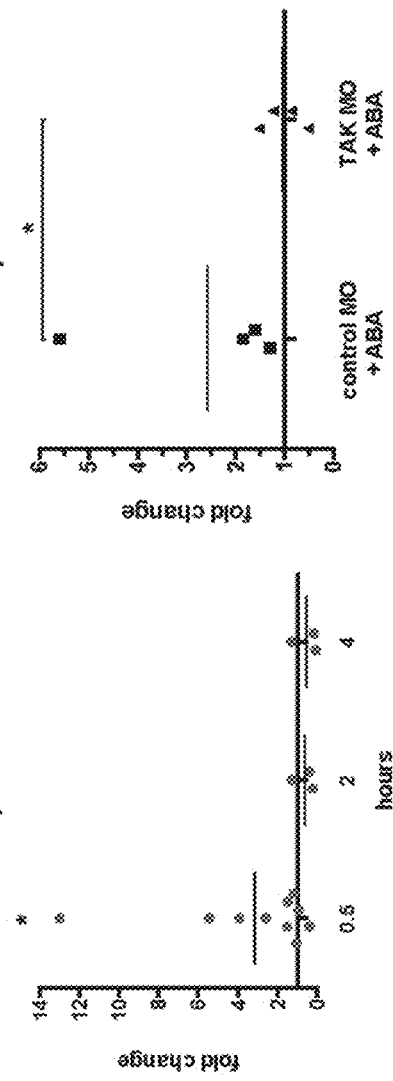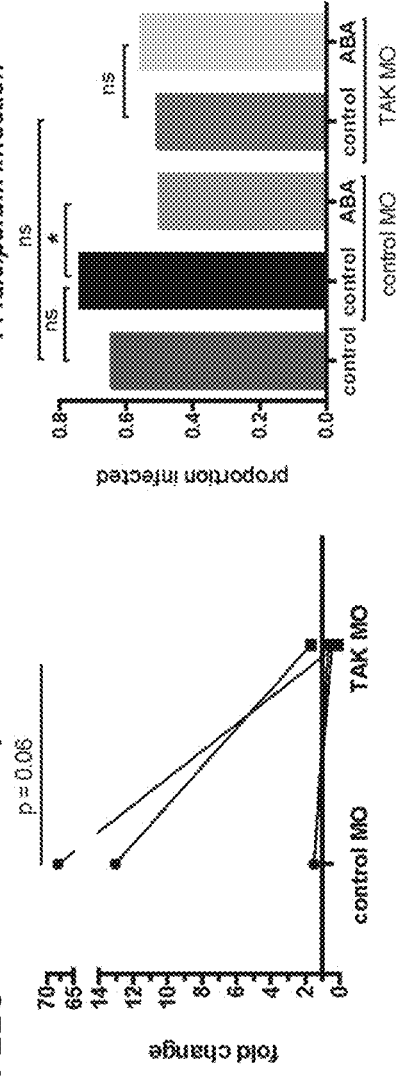

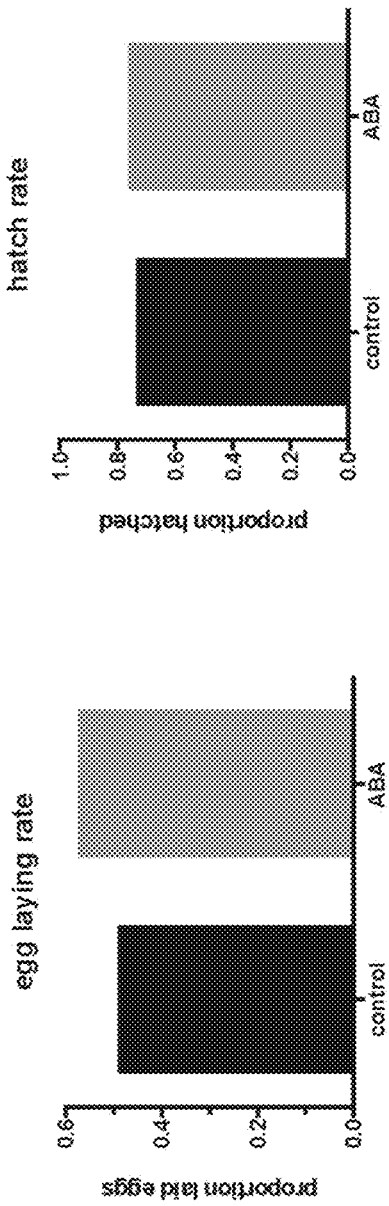
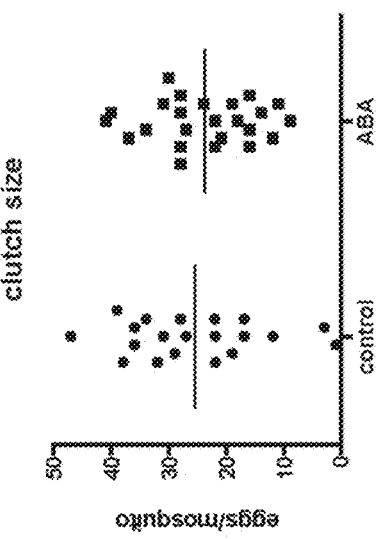
FIG. 18A
FIG. 18B
FIG. 18C

USE OF ABSCISIC ACID FOR THE PREVENTION AND TREATMENT OF MALARIA

CROSS-REFERENCE TO RELATED APPLICATIONS

This application claims benefit of U.S. Provisional Application No. 62/242,587, filed Oct. 16, 2015, which is incorporated by reference in its entirety.

FIELD

The present disclosure provides methods for treating or preventing malaria by administration of abscisic acid, analogs or pharmaceutical salts thereof to a mammalian subject infected with or at risk of exposure to *Plasmodium*. In some aspects, the therapeutic and prophylactic regimens of the present disclosure are effective in reducing one or more of parasitemia, gametocytemia, disease severity and disease pathology in a mammalian subject, and/or reducing transmission of *Plasmodium* by a mosquito vector.

BACKGROUND

Malaria is an infectious disease caused by protozoan parasites in the genus *Plasmodium* that are transmitted from host to host by mosquitoes. Malaria initially manifests with mild to severe symptoms including: chills, fever, fatigue, headache, and nausea. Later symptoms include severe anemia, and blood clotting, which can lead to brain damage and other complications, and death. Although five species of *Plasmodium* (*P. falciparum, P. vivax, P. ovale, P. malariae,* and *P. knowlesi*) can infect humans, the majority of malarial deaths are caused by *P. falciparum* and *P. vivax*.

Nearly half of the world's population is at risk for malaria. The World Health Organization (WHO) estimates that about 200 million cases and about 600,000 deaths occur each year (WHO, World Malaria Report, 2014). Increasing drug resistance has intensified the need for new therapeutics. The development of drugs that can target more than one parasite stage has been identified as an important strategy for controlling malaria. Particularly desirable are treatments with transmission-blocking properties.

BRIEF SUMMARY

In some embodiments, the present disclosure provides methods for treating or preventing malaria comprising: administering a composition comprising purified or synthetic abscisic acid (ABA), an analog thereof or a pharmaceutical salt thereof to a mammalian subject in need thereof under conditions effective for treating or preventing malaria. In some embodiments, the subject is not infected with *P. falciparum, P. vivax, P. ovale, P. malariae,* or *P. knowlesi,* but is at risk of infection. In some embodiments, the uninfected subject at risk of infection resides in a malaria endemic area or plans to visit a malaria endemic area. In preferred embodiments, preventing malaria comprises protecting the subject from developing parasitemia for duration of the administering step. In some embodiments, the administering step extends from 1-14 days before the risk of infection has started to 1-30 days after the risk of infection has ended. In areas where *Plasmodium* transmission is seasonal due to a predictable rainy season, the administering step extends throughout the rainy season. In other embodiments, the subject is infected with *P. falciparum, P. vivax, P. ovale, P. malariae,* or *P. knowlesi*. In some embodiments, the *Plasmodium* is *P. falciparum* or *P. vivax*. In a preferred embodiment, the *Plasmodium* is *P. falciparum*. In preferred embodiments, treating malaria comprises alleviating a symptom of malaria experienced by the subject. In some embodiments, the composition is administered one, two, three, four or five times per day for a duration of one, two, three or four months. In other embodiments, the composition is administered one, two or three times per week. In some embodiments, the composition is administered for a duration of six, nine, or twelve months or longer. In some embodiments, the subject is at a high risk of death from *Plasmodium* infection (e.g., children under the age of 5, subjects in need of surgery or transfusion, subjects infected with HIV-1 or HIV-2, subjects with HIV-AIDS, etc.). In some embodiments, the methods further comprise administering an effective amount of an additional antimalarial drug to the subject. In some embodiments, the additional antimalarial drug comprises one or more compounds of the antimalarial classes selected from the group consisting of amino alcohols, aminoquinolines, antibiotics, antifolates, endoperoxides, sulfonamides, and others. In some embodiments, the abscisic acid, analog thereof or pharmaceutical salt thereof is administered to the subject at a dose of between 0.1 mg/kg/day and 10,000 mg/kg/day, preferably between 1 mg/kg/day and 1,000 mg/kg/day. In some embodiments, the composition is administered orally, while in others the composition is administered by injection.

In addition to and in combination with embodiments described above, the therapeutic and prophylactic regimens of the present disclosure are effective in reducing one or more of parasitemia, gametocytemia, disease severity and disease pathology in a mammalian subject, and/or reducing transmission of *Plasmodium* by an *Anopheles* mosquito. Specifically, the present disclosure further provides methods for reducing *Plasmodium* parasitemia in a mammalian subject, comprising: administering a composition comprising purified or synthetic abscisic acid, an analog thereof or a pharmaceutical salt thereof to a mammalian subject in need thereof under conditions effective for reducing *Plasmodium* parasitemia in the subject. In some embodiments, the conditions are further effective for reducing *Plasmodium* gametocytemia in the subject. Additionally, the present disclosure provides methods for reducing one or both of disease severity and disease pathology in a mammalian subject with malaria, comprising: administering a composition comprising purified or synthetic abscisic acid, an analog thereof or a pharmaceutical salt thereof to the mammalian subject under conditions effective for reducing one or both of disease severity and disease pathology in the subject. Reducing disease severity comprises reducing a sign or symptom of malaria, while reducing disease pathology comprises reducing changes in tissues or bodily fluids of a subject as a consequence of infection by *Plasmodium*.

Moreover and in combination with embodiments of the preceding paragraphs, the present disclosure provides methods for reducing transmission of *Plasmodium* by an *Anopheles* mosquito, comprising: administering a composition comprising purified or synthetic abscisic acid, an analog thereof or a pharmaceutical salt thereof to a mammalian subject infected with *Plasmodium* under conditions effective for reducing transmission of the *Plasmodium* ingested by the mosquito in blood of the subject. In some embodiments, the *Plasmodium* is *P. falciparum, P. vivax, P. ovale, P. malariae,* or *P. knowlesi*. In some embodiments, the *Plasmodium* is *P. falciparum* or *P. vivax*. In a preferred embodiment, the *Plasmodium* is *P. falciparum*.

Also, and in combination with other embodiments detailed herein, the present disclosure provides pharmaceutical compositions comprising a purified or synthetic abscisic acid, an analog thereof or pharmaceutical salt thereof, an additional antimalarial agent, and one or both of a pharmaceutically acceptable excipient and carrier, wherein the abscisic acid, analog or salt and the additional antimalarial agent are present in amounts effective to treat or prevent malaria in a mammalian subject. In some embodiments, the additional antimalarial drug comprises one or more compounds of the antimalarial classes selected from the group consisting of amino alcohols, aminoquinolines, antibiotics, antifolates, endoperoxides, sulfonamides, and others. In specific embodiments, the composition is formulated for enteral or parenteral administration, preferably by oral administration or by injection (e.g., intravenous, intramuscular, or subcutaneously).

In some embodiments, the mosquitos are of a species selected from the group consisting of *Anopheles* (Cellia) *aconitus* Dönitz 1902; *Anopheles* (Nyssorhynchus) *albimanus* Wiedemann, 1820; *Anopheles* (Nyssorhynchus) *albitarsis* species complex; *Anopheles* (Cellia) *annularis* van der Wulp, 1884; *Anopheles* (Nyssorhynchus) *aquasalis* Curry, 1932; *Anopheles* (Cellia) *arabiensis* Patton, 1905; *Anopheles* (Anopheles) *atroparvus* van Thiel, 1927; *Anopheles* (Cellia) *balabacensis* Baisas, 1936; *Anopheles* (Anopheles) *barbirostris* species complex; *Anopheles* (Cellia) *culicifacies* species complex; *Anopheles* (Nyssorhynchus) *darlingi* Root, 1926; *Anopheles* (Cellia) *dirus* species complex; *Anopheles* (Cellia) *farauti* species complex; *Anopheles* (Cellia) *flavirostris* (Ludlow, 1914); *Anopheles* (Cellia)*fluviatilis* species complex; *Anopheles* (Anopheles) *freeborni* Aitken, 1939; *Anopheles* (Cellia) *funestus* Giles, 1900; *Anopheles* (Cellia) *gambiae* Giles, 1902; *Anopheles* (Cellia) *koliensis* Owen, 1945; *Anopheles* (Anopheles) *labranchiae* Falleroni, 1926; *Anopheles* (Anopheles) *lesteri* Baisas & Hu, 1936 (formerly An. anthropophagus in China); *Anopheles* (Cellia) *leucosphyrus* and *Anopheles* (Cellia) *latens*; *Anopheles* (Cellia) *maculatus* Group; *Anopheles* (Nyssorhynchus) *marajoara* Galvão & Damasceno, 1942; *Anopheles* (Cellia) *melas* Theobald, 1903; *Anopheles* (Cellia) *merus* Dönitz, 1902; *Anopheles* (Anopheles) *messeae* Falleroni, 1926; *Anopheles* (Cellia) *minimus* species complex; *Anopheles* (Cellia) *moucheti* Evans, 1925; *Anopheles* (Cellia) *nili* species complex; *Anopheles* (Nyssorhynchus) *nuneztovari* species complex; *Anopheles* (Anopheles) *pseudopunctipennis* species complex; *Anopheles* (Cellia) *punctulatus* species complex; *Anopheles* (Anopheles) *quadrimaculatus* Say, 1824; *Anopheles* (Anopheles) *sacharovi* Favre, 1903; *Anopheles* (Cellia) *sergentii* species complex; *Anopheles* (Anopheles) *sinensis* species complex; *Anopheles* (Cellia) *stephensi* Liston, 1901; *Anopheles* (Cellia) *subpictus* species complex; *Anopheles* (Cellia) *sundaicus* species complex; and *Anopheles* (Cellia) *superpictus* Grassi, 1899. In some embodiments, the mosquitoes are *Anopheles stephensi*.

BRIEF DESCRIPTION OF THE DRAWINGS

FIG. 3A-D depict the histologic effects of ABA treatment in the liver and spleen. FIG. 3A shows a measure of sinusoidal leukocytes in the liver. FIG. 3B shows a measure of adhered leukocytes in the liver. FIG. 3C shows a measure of microabscesses in the liver. FIG. 3D shows lymphoid hyperplasia of the spleen.

FIG. 7A-B depict the effect of ABA on *P. falciparum* asexual growth (FIG. 7A) and gametocytogenesis in vitro (FIG. 7B).

FIG. 8A shows infection prevalence in *A. stephensi*, relative to control. FIG. 8B shows mean oocysts per midgut of *P. falciparum*-infected mosquitoes. FIG. 8C shows AsNOS transcript levels in the midguts of ABA-treated mosquitoes relative to controls. FIG. 8D shows the infection prevalence of *P. falciparum* after provision of ABA, ABA and 1 mg/ml NOS inhibitor Nω-Nitro-L-arginine methyl ester (L-NAME), the inhibitor alone, or with an equivalent volume of ABA and inhibitor diluents as a control.

FIG. 9A-D depict defensin (FIG. 9A), LRIM (FIG. 9B), APL1 (FIG. 9C), and TEP1 (FIG. 9D) mRNA levels after ABA treatment.

FIG. 11A-D illustrate that ABA decreases *P. falciparum* infection by increasing TAK phosphorylation. FIG. 11A shows the fold change in levels of TAK phosphorylation in ABA-supplemented parasite-fed mosquito midguts compared to controls. Each dot represents one replicate of 15 pooled midguts. FIG. 11B shows the fold change in levels of TAK phosphorylation in ABA-supplemented parasite-fed mosquito midguts treated with a control or TAK-targeted morpholino (MO). FIG. 11C shows the fold change in expression of NOS in ABA-supplemented parasite-fed mosquito midguts fed either control- or TAK-morpholinos. FIG. 11D shows the *P. falciparum* infection intensity in mosquitoes fed no morpholinos, control morpholinos, or TAK-targeted morpholinos followed by a control or ABA-supplemented infected bloodmeal. Phosphorylated TAK levels were analyzed by one sample t-test, NOS expression by Wilcoxon matched-pairs signed rank test, and infection prevalence by Fisher's exact test. * p<0.05.

FIG. 17A is a survival curve of mosquitoes provided weekly control or ABA-supplemented uninfected bloodmeals and maintained on 3% sucrose solution. FIG. 17B is a survival curve of *P. falciparum*-infected mosquitoes provided control or ABA-supplemented weekly bloodmeals. Infection status was determined by detection of PfCOX in individual mosquitoes by qRT-PCR. Data were analyzed by log-rank test and Gehan-Breslow-Wilcoxon test.

FIG. 18A-C illustrate that ABA supplementation does not alter egg production or viability. FIG. 18A shows the proportion of fully engorged mosquitoes that laid one or more eggs within two days of feeding on control or ABA-supplemented uninfected blood. n=41-42. FIG. 18B shows the proportion of eggs that hatched to first instar larvae. The egg laying rate and hatch rate were analyzed using Fisher's exact test. FIG. 18C shows the number of eggs laid after a single control or ABA-supplemented bloodmeal. Each dot represents the clutch size of a single mosquito. Clutch size was analyzed by unpaired t-test.

FIG. 27A shows fold changes in quantity of each antibody isotype in pooled plasma from control and ABA-supplemented day 13 infected mice. FIG. 27B shows parasitemia over time of mice injected with plasma from control or ABA-treated mice 24 hours before infection with *P. yoelii* 17XNL. Data were analyzed by unpaired t-test. n=3-4 # $p<0.1$ * $p<0.05$.

FIG. 28A shows parasitemia over time in C57Bl/6 mice with and without ABA supplementation. FIG. 28B shows parasitemia over time in casp1−/− mice with and without ABA supplementation. 4-5 mice were used per treatment group. Data were analyzed by unpaired t-test. # p<0.1 * p<0.05.

DETAILED DESCRIPTION

Figure 1B:
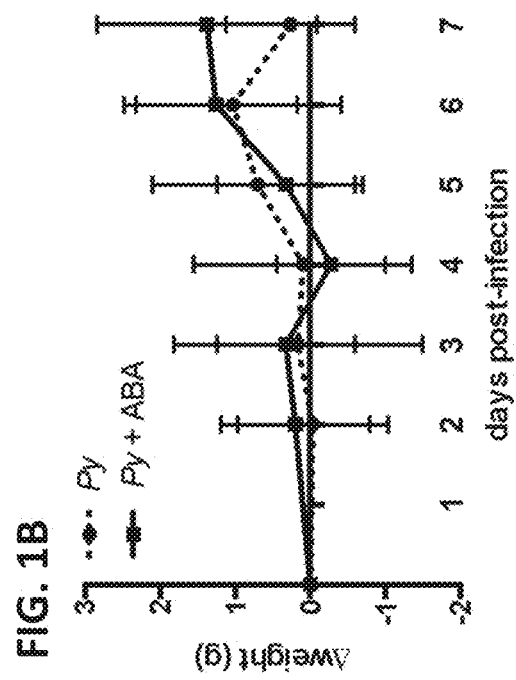
FIG. 1A-B depict the effect of abscisic acid (ABA) supplementation on water consumption (FIG. 1A) and body weight (FIG. 1B) of infected mice and controls.

During development of the present disclosure, abscisic acid (ABA) was found to be able to reduce *Plasmodium* infection, disease pathology and transmission. Daily supplementation of ABA in drinking water reduced parasite levels in blood, improved spleen and liver health, and reduced transmission to mosquitoes in a mouse malaria model. This supplementation also increased ABA levels in the blood, which could be ingested by mosquitoes. When ABA was added to blood containing the human malaria parasite *Plasmodium falciparum* prior to feeding to mosquitoes, parasite infection success relative to control mosquitoes was significantly reduced. ABA is present in many fruits and vegetables that are part of the human diet and is therefore safe for human consumption. Thus, ABA is suitable for reducing *Plasmodium* transmission to human subjects. Additionally, malaria complications such as cerebral pathology and liver dysfunction are expected to be mitigated by ABA supplementation.

As detailed herein, oral ABA supplementation reduces *P. yoelii* parasitemia and gametocytemia, disease pathology, and parasite transmission to the mosquito *A. stephensi*. Hence, ABA supplementation limited growth and development of *P. yoelii* life stages in two different hosts: asexual growth and gametocyte formation in the mammalian host and survival to oocyst formation in the mosquito host. The lack of a direct effect on *P. falciparum* asexual growth or gametocyte formation in vitro suggests that ABA alters the biology of both the mammalian and insect hosts to limit infection and transmission.

In mammals, ABA can be pro- or anti-inflammatory depending on context. For example, treatment with ABA can activate human macrophages in vitro, stimulating phagocytosis and the release of reactive nitrogen and oxygen species (Bruzzone et al., supra, 2007; and Bodrato et al., *J Biol Chem*, 2009, 284:14777-87). In contrast, ABA supplementation in a mouse model of inflammatory bowel disease (IBD) reduced epithelial erosion and leukocyte infiltration. In this context, ABA supplementation has been proposed as a treatment for IBD due to its ability to limit harmful inflammation (U.S. Pat. No. 8,367,727 to Bassaganya-Riera et al.).

The effect of ABA on inflammatory pathology in the mouse liver and spleen described herein could derive from a direct, restorative effect of ABA on these tissues or from significantly reduced parasitemia. In a mouse model of influenza, ABA treatment decreased vascular infiltrates, but had no effect on viral load (Hontecillas et al., *J Nutr Biochem*, 2013, 24:1019-1027). During development of the present disclosure, a reduction in leukocyte infiltration into the liver was observed with ABA treatment in the absence of infection, indicating that ABA can directly affect some host responses independently of its effect on pathogen load. The reduction in pathology in the mouse model is likely due to a combination of the direct effects of ABA on host tissues and the reduction in parasitemia.

The reduction in liver and spleen pathology corresponded to increased PPARγ expression in both tissues on day 7 of infection. The reduction in leukocyte adherence in the liver with ABA treatment corresponds with increased PPARγ transcript levels. Thus, ABA supplementation, through these beneficial effects on PPARγ, is expected to ameliorate symptoms of severe or complicated malaria.

The reduction in liver and spleen pathology also corresponded to decreased NOS expression in both tissues on day 7 of infection. The impact of NOS expression in malaria is tissue- and time-specific. In the context of the observed reduction in tissue pathology and increased PPARγ transcript levels, it is likely that decreased NOS expression in the liver and spleen of ABA-supplemented mice on day 7 of infection reflects recovery from inflammation.

In contrast to later resolution of inflammation in the mouse, ingestion of ABA by the mosquito induced high levels of AsNOS expression within 4-6 hours after infection, an early period of infection that coincides with the presence of newly formed ookinetes in the midgut lumen. Coincident with this response were induced levels of defensin and APL1 transcripts, indicating that ABA signaling regulates NF-κB-dependent gene expression. Given the significant reduction in parasitemia in ABA-treated mice by 3-4 days post-infection, ABA is thought to promote early inflammatory responses in both hosts to reduce parasite development and to promote restoration from inflammation as observed in the mouse.

Abscisic Acid (ABA)

The systematic *International Union of Pure and Applied Chemistry* (IUPAC) name of ABA is (2Z,4E)-5-[(1S)-1-hydroxy-2,6,6-trimethyl-4-oxocyclohex-2-en-1-yl]-3-methylpenta-2,4-dienoic acid. ABA is also referred to as 2,4-Pentadienoic acid, 5-[(1S)-1-hydroxy-2,6,6-trimethyl-4-oxo-2-cyclohexen-1-yl]-3-methyl-, (2Z,4E)-, or simply abscisin II or dormin. As used herein, the term ABA includes but is not limited to (±)-abscisic acid (CAS Registry Number 14375-45-2), (+)-abscisic acid (CAS Registry Number of ABA is 21293-29-8), 2-cis,4-trans-abscisic acid (CAS Registry Number 14375-45-2), and (−)-cis,trans-abscisic acid (CAS Registry Number 14398-53-9).

The isoprenoid ABA was originally characterized as a plant hormone controlling leaf abscission, but has since been detected in a wide variety of eukaryotes including mammals (Bruzzone et al., *Proc Natl Acad Sci USA*, 2007, 104:5759-64), sponges, and the apicomplexan parasite *Toxoplasma gondii*. In these organisms, ABA functions in immune and metabolic processes, including desiccation tolerance in plants, heat stress response in sponges, and insulin release in humans (Bruzzone et al., *FASEB J*, 2011, 26:1251-60). ABA also increases cell proliferation, regulating regeneration in hydroids and expansion of human mesenchymal stem cells (Puce et al., *J Biol Chem*, 2004, 279:39783-8 and Scarfi et al., *Stem Cells*, 2008, 26:2855-64.).

Analogs and Pharmaceutical Salts of Abscisic Acid (ABA)

In addition to ABA, the present disclosure provides analogs and pharmaceutical salts of ABA for use in the methods and compositions of the present disclosure. Specifically, non-toxic salts, active esters, active isomers, active metabolites, derivatives, structurally-related compounds, and mixtures thereof are suitable substitutes for ABA. Non-toxic salts include, for example, alkyl esters having from 1 to 6 carbon atoms in the alkyl group, as well as mono-, di- and tri-glycerides, and mixtures thereof. Active isomers of abscisic acid include geometrical isomers and its non-toxic salts, e.g., sodium, potassium, calcium, and magnesium salts, and its active esters, e.g., alkyl esters having from 1 to 6 carbon atoms in the alkyl group, as well as mono-, di- and tri-glycerides, and mixtures thereof. Active optical isomers of abscisic acid include the (+)-enantiomer and the (−)-enantiomer and its non-toxic salts, e.g., sodium, potassium, calcium, and magnesium salts, and its active esters, e.g., alkyl esters having from 1 to 6 carbon atoms in the alkyl group, as well as mono-, di- and tri-glycerides, and mixtures thereof. Active metabolites of abscisic acid include oxygenated ABA analogs, including but not limited to, 8'-hydroxyABA, (+)-7'-hydroxyABA, 2'3'-dihydroABA, 8'-hydroxy-2',3'-dihydroABA and its non-toxic salts, e.g., sodium, potassium, calcium, and magnesium salts, and its active esters, e.g., alkyl esters having from 1 to 6 carbon atoms in the alkyl group, as well as mono-, di- and tri-glycerides, and mixtures thereof. Structurally related compounds, include but are not limited to, compounds containing conjugated double bonds (e.g., conjugated dienes, trienes and tetraenes) in the unsaturated side chain and compounds containing a trimethylcyclohexene ring with or without hydroxy moieties.

Abscisic acid may be a substantially pure single chemical compound or a mixture of one or more abscisic acid compounds as described above. For example, the abscisic acid may be in the form of an extract obtainable or obtained from plant extracts, either directly or following one or more steps of purification or ABA can be chemically synthesized. The ABA used in the described methods may be in a free acid form or bound chemically through ester linkages. In its natural form, ABA is heat stable. ABA may be used in its natural state or in a dried and powdered form. Other structurally related compounds are known in the art; for example, as disclosed by: Han et al., *Bioorganic & Medicinal Chemistry*, 2015, 23: 6210-6217; Abrams et al., *Plant Physiol*, 1997, 114:89-97; Grozio, et al., *Biochemical and Biophysical Research Communications* 2011, 415:696-701; Lynch, *Gen Pharmac*, 1991, 22:5, 895-901; and Todoroki et al., *Bioorganic & Medicinal Chemistry*, 2011, 19:1743-1750, details of the related compounds described in these publications is hereby incorporated by reference.

In some embodiments ABA, and its derivatives, is in the form of a pharmaceutically acceptable salt. For instance, if the ABA, or derivative thereof, has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., formic acid, acetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). Alternatively, if the ABA, or derivative thereof, has an acidic group, such as for example, a carboxylic acid group, it can form salts with metals, such as alkali and earth alkali metals (e.g., sodium, lithium, potassium, calcium, magnesium, zinc), ammonia, organic amines (e.g., trimethylamine, triethylamine, pyridine, picoline, ethanolamine, diethanolamine, triethanolamine), or basic amino acids (e.g., arginine, lysine and ornithine). For example, the free acid form of ABA may be converted into a non-toxic salt, such as sodium, potassium or calcium salts, by reacting chemically equivalent amounts of the free acid form with an alkali hydroxide at a basic pH.

ABA Compositions

The present disclosure also provides pharmaceutical compositions comprising ABA, an analog thereof or a pharmaceutical salt thereof, and one or both of a pharmaceutically acceptable excipient and carrier, wherein the ABA, the analog or the salt is present in an amount effective to treat or prevent malaria in a mammalian subject. A therapeutically effective amount of ABA or a pharmaceutical salt thereof, may vary depending upon the route of administration and dosage form. Effective amounts of ABA or a pharmaceutical salt thereof, typically fall in the range of about 0.0001 to 1000 mg/kg/day, typically 0.001 to 100 mg/kg/day, and more typically in the range of about 0.01 up to 10 mg/kg/day. In some embodiments, ABA or a pharmaceutical salt thereof, is administered to a subject in an amount less than any of the following daily doses (mg/kg): 100, 50, 10, 5.0, 1.0, 0.5 or 1. In some embodiments, ABA or a pharmaceutical salt thereof, is administered to a subject in an amount greater than any of the following daily doses (mg/kg): 0.001, 0.005, 0.01, 0.05, 0.1 or 0.5. That is, the daily dose (mg/kg) can be any of a range of having an upper limit of 100, 50, 10, 5.0, 1.0, 0.5 or 1, and an independently selected lower limit of 0.001, 0.005, 0.01, 0.05, 0.1 or 0.5, wherein the lower limit is less than the upper limit. Thus, the actual amount per day for an adult mammal weighing 70 kg is typically between 0.07 and 7,000 mg, or more typically between 0.7 and 700 mg, where this amount can be administered as a single dose per day or as a series of part-doses (such as, for example, two, three, four, five or six) per day, so that the total daily dose is the same.

Typically, ABA or a pharmaceutical salt thereof, is provided to a subject in an amount sufficient to provide a formulation that exhibits a high therapeutic index. The therapeutic index is the dose ratio between toxic and therapeutic effects, which can be expressed as the ratio between LD50 and ED50. The LD50 is the dose lethal to 50% of the population and the ED50 is the dose therapeutically effective in 50% of the population. The LD50 and ED50 are determined by standard pharmaceutical procedures in animal cell cultures or experimental animals.

A therapeutically effective amount of ABA or the like can be administered to a subject, including mammals and humans, by enteral or parenteral routes as known in the art. The most appropriate mode of administration would be easily determined by a person of skill in the art, taking into account various factors such as subject age, size, medical background, stage of malaria infection and/or likelihood of contracting malaria, and likelihood of response to ABA. In preferred embodiments, the ABA composition is administered orally or by injection.

For oral administration, the effective amount of ABA may be administered in, for example, a solid, semi-solid, liquid, or gas state. To formulate the ABA of the present invention into tablets, capsules, powders, granules, solutions, or suspensions, the ABA compound is preferably mixed with a binder, a disintegrating agent and/or a lubricant. If necessary, the resultant composition may be mixed with a diluent, a buffer, an infiltrating agent, a preservative and/or a flavor. Examples of the binder include crystalline cellulose, cellulose derivatives, cornstarch, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used. For oral administration, the purified ABA may be mixed with water prior to administration. ABA may also be administered to a subject in need thereof as a nutritional additive, either as a food or nutraceutical supplement.

For administration by injection, the ABA compound may be injected intravenously, intramuscularly, or subcutaneously. Medicinal drugs for such injection may be prepared by dissolving, suspending or emulsifying the ABA into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added.

ABA may be administered to a subject, including mammals and humans, in need thereof as a pharmaceutical or veterinary composition, such as tablets, capsules, solutions, or emulsions. In a preferred embodiment of the invention, the free acid form of ABA is administered. However, administration of other forms of ABA, including but not limited to esters thereof, pharmaceutically-suitable salts thereof, metabolites thereof, structurally related compounds thereof, analogs thereof, and combinations thereof, in a single dose or a multiple dose, are also within the scope of the present disclosure.

A preferred pharmaceutical composition is a single dosage form for oral administration, such as a pill, capsule, tablet, caplet, powder, liquid, or the like. A pharmaceutical composition in the form of a tablet suitable for oral administration can comprise one or more pharmaceutically acceptable carriers and/or excipients suitable (e.g., inactive ingredients). Exemplary carriers include but are not limited to lactose, cellulose (for example microcrystalline cellulose), and mannitol. Exemplary excipients include but are not limited to binding agents such as hydroxypropylmethylcellulose or povidone (polyvinylpyrollidone), lubricants such as magnesium stearate, and disintegrants such as sodium starch glycollate, croscarmellose sodium, or crospovidone (cross-linked polyvinylpyrollidone). As with the forms for use in medical settings, typical additives can be included, such as colorants, flavorants, binders, gums, and the like. The present disclosure further provides a use of ABA or compositions comprising ABA for treatment or prophylaxis of vector-borne diseases, such as malaria, in a subject by way of nutritional supplements, such as through dietary supplements.

Combination Therapies

The present disclosure further provides methods for treating or preventing malaria comprising administering a purified or synthetic ABA, an analog thereof or a pharmaceutical salt thereof, and an additional antimalarial (e.g., a compound that is not ABA, an analog or a salt thereof) to a subject in need thereof under conditions suitable for treating or preventing malaria. In some embodiments, the ABA, analog or salt, and the antimalarial are present in a single formulation, while in other embodiments the ABA, analog or salt, and the antimalarial are present in separate formulations. In some embodiments, the additional antimalarial comprises one or more compounds of the antimalarial classes selected from the group consisting of amino alcohols, aminoquinolines, antibiotics, antifolates, endoperoxides, sulfonamides, and others (see, e.g., Delves et al., *PLoS Medicine*, 2012, 9(2): e1001169; Travassos and Laufer, UpToDate® [network-based, clinical decision support resource of Wolters Kluwer Health] 2015; and WHO, Guidelines For The Treatment Of Malaria, $3^{rd}$ edition, 2015).

In particular, the additional antimalarial compound(s) may be aminoquinolines (including, but not limited to, amodiaquine, naphthoquine, AQ-13, tert-butyl isoquine, hydroxycholoquine, pyronaridine, diethylprimaquine, bulaquine, primaquine, tafenoquine, piperaquine, NPC-1161B, and chloroquine), antibiotics (including, but not limited to, azithromycin, trimethoprim, trimethoprim-sulphamethoxazole, tetracycline, mirincamycin, doxycycline, thiostrepton, fosmidomycin, and clindamycin), endoperoxides (including, but not limited to, artemether, arteether, artesunate, OZ439, OZ277, artemisinin, artemisone, and dihydroartemisinin), antifolates (such as pyrimethamine, proguanil, dapsone, cycloguanil, P218, and chlorproguanil), sulfonamides (such as sulfadoxine, sulfadiazine, and sulfmethoxazole), amino alcohols (such as lumefantrine, halofantrine, mefloquine, quinine and quinidine), or other antimalarial drugs (including, but not limited to, DSM1, DSM265, P218, BCX4945, synthetic peroxides, methylene blue, riboflavin, pentamidine, DHEA, cycloheximide, atovaquone, deferoxamine, and N-acetyl-D-penicillamine). In some embodiments, the combination therapy includes a fixed-dose artemisinin combination therapy. In some aspects, the artemisinin combination therapy is comprised of purified or synthetic ABA, an analog thereof or a pharmaceutical salt thereof, as well as one or more of artemether, artesunate, dihydroartemisinin, artemisone, and artemisinin. In other aspects, the artemisinin combination therapy is comprised of a purified or synthetic ABA, an analog thereof or a pharmaceutical salt thereof, and one of the group consisting of artemether-lumefantrine, artesunate-amodiaquine, artesunate-mefloquine, artesunate-sulfaodoxine-pyrimethamine, and dihydroartemesinin-piperquine.

In some embodiments, the additional antimalarial counteracts the malarial parasite at the same life stage(s) as the ABA or a pharmaceutical salt thereof. In other embodiments, the additional antimalarial counteracts the malarial parasite at a different life stage from the ABA or a pharmaceutical salt thereof.

Treatment of Infections by Other Protozoan Parasites

In other embodiments, the use of purified or synthetic ABA, an analog thereof or a pharmaceutical salt thereof, is applied to diseases caused by other intracellular parasitic protozoa. A large number of protozoal pathogens spend a portion of their life cycle in a mammalian host (e.g., human). Diseases caused by infection with other intracellular parasitic protozoa are also treated or prevented by the ABA, analog or salt. In particular, the present disclosure provides ABA, an analog or a salt, for use thereof in mammalian subjects infected with a protozoan parasite selected from the group consisting of *Giardia lamblia, Cryptosporidium parvum, Cyclospora cayetanensis, Entamoeba histolytica, Trichomonas tenax, Trichomonas hominis, Trichomonas vaginalis, Trypanosoma brucei gambiense, Trypanosoma brucei rhodesiense, Trypanosoma cruzi, Leishmania donovani, Leishmania tropica, Leishmania braziliensis, Pneumocystis pneumonia, Toxoplasma gondii, Theileria lawrenci,* and *Theileria parva*. In preferred embodiments, the protozoan parasite is vectored by an arthropod (e.g., sand fly-transmitted *Leishmania*, tick-borne *Babesia microti*, kissing bug-transmitted *Trypanosoma cruzi*, tsetse-transmitted *Trypanosoma brucei*). In some embodiments, the disease is Chagas disease, caused by infection with *Trypanosoma cruzi*. In general, the present disclosure provides methods for use of the ABA, analog or salt in hosts infected with a protozoan parasite.

General Techniques

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (Gait, ed., 1984); Animal Cell Culture (Freshney, ed., 1987); Handbook of Experimental Immunology (Weir & Blackwell, eds.); Gene Transfer Vectors for Mammalian Cells (Miller & Calos, eds., 1987); Current Protocols in Molecular Biology (Ausubel et al., eds., 1987); PCR: The Polymerase Chain Reaction, (Mullis et al., eds., 1994); Current Protocols in Immunology (Coligan et al., eds., 1991); The Immunoassay Handbook (Wild ed., Stockton Press NY, 1994); Bioconjugate Techniques (Hermanson, ed., Academic Press, 1996); and Methods of Immunological Analysis (Masseyeff, Albert, and Staines, eds., Weinheim: VCH Verlags gesellschaft mbH, 1993).

Definitions

As used herein, the singular form "a", "an", and "the" includes plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting" and/or "consisting essentially of" aspects and embodiments.

Administration of ABA, an analog thereof or a pharmaceutical salt thereof, and an additional antimalarial drug includes simultaneous (concurrent) and consecutive administration in any order.

An "effective amount of" or "under conditions effective for" refers to administration of ABA, an analog or a pharmaceutical salt thereof, in an amount sufficient to carry out a specifically stated purpose. An "effective amount" may be determined empirically and in a routine manner, in relation to the stated purpose.

The term "therapeutically effective amount" refers to an amount of an agent (e.g., ABA, analog thereof or a pharmaceutical salt thereof) effective to "treat" a disease or disorder in a subject (e.g., a mammal such as a human). In the case of malaria, the therapeutically effective amount of the agent reduces a sign or symptom of malaria. Symptoms of malaria include but are not limited to headache, fever, shivering, joint pain, vomiting, hemolytic anemia, jaundice, hemoglobin in the urine, retinal damage, and convulsions. One notable symptom of malaria is paroxysm, which is a cyclical occurrence (every 24-72 hours) of coldness and shivering followed by fever and sweating. The World Health Organization classifies malaria is classified as "severe" when the subject has experienced any of the following: decreased consciousness, significant weakness, inability to eat, two or more convulsions, low blood pressure, difficulty breathing, circulatory shock, kidney failure or hemoglobin in the urine, bleeding problems, or hemoglobin less than 50 g/L (5 g/dL), pulmonary edema, blood glucose less than 2.2 mmol/L (40 mg/dL), blood acidosis or lactate levels of greater than 5 mmol/L, greater than 100,000 parasites per microliter of blood in low-intensity transmission areas or 250,000 per microliter of blood in high-intensity transmission areas. When the subject has not experienced any signs of severe malaria, the disease is considered "uncomplicated." The term "cerebral malaria" refers to severe malaria associated with *Plasmodium falciparum* infection and accompanied by neurological symptoms such as abnormal posturing, nystagmus, conjugate gaze palsy, opisthotonus, seizures, or coma.

As used herein, the terms "isolated" refers to a compound (e.g., ABA or the like) that is removed from its natural environment (e.g., separated). "Isolated" compounds are at least 50% free, preferably 75% free, more preferably at least 90% free, and most preferably at least 95% (e.g., 95%, 96%, 97%, 98%, or 99%) free from other components with which they are naturally associated. The term "isolated" encompasses ABA purified from plants, as well as ABA synthesized chemically.

The terms "treating" or "treatment" of a disease refer to executing a protocol, which may include administering one or more drugs to an individual (human or otherwise), in an effort to alleviate signs or symptoms of the disease. Thus, "treating" or "treatment" does not require complete alleviation of signs or symptoms, does not require a cure, and specifically includes protocols that have a measurable effect on the individual.

As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The terms "reduce" and "reduction" as used in reference to biological function (e.g., parasite development, etc.) refer to a measurable decrease in the function by preferably at least 50%, more preferably at least 75% and most preferably at least 90%. Depending upon the function, the reduction may be from 10-fold to 1,000,000-fold, or from 10, 100 or 1000-fold to 10,000, 100,000 or 1,000,000-fold.

EXAMPLES

Materials and Methods

Animals, Infection, and Histology.

6-8 week old female CD1 mice (Jackson) were housed four to a cage and provided with unsupplemented water or water supplemented with 2.56 mM (±)-abscisic acid (CAS Registry Number 14375-45-2) obtained from Sigma-Aldrich (Catalog No. A1049). Water and supplemented water were changed daily. On day 3 of supplementation, mice were injected intraperitoneally with $5 \times 10^6$ *P. yoelii* 17XNL-infected RBCs. Mouse weight, water consumption per cage, and parasitemia were monitored daily. Parasitemia was determined from thin blood films stained with Giemsa. Parasitemia was measured as the percentage of infected RBCs divided by total RBCs, while gametocytemia was measured as the proportion of gametocyte-containing RBCs of total infected RBCs. Four mice were used per group in replicated studies. Daily parasitemias and gametocytemias were analyzed by unpaired t-test.

Mice were euthanized on day 7 post-infection. Blood was collected by heart puncture, spun at 8,000 rpm for 8 minutes and the plasma collected for ABA quantification. Livers and spleens were collected, retained in 10% formalin for 24 hours and then stored in 70% ethanol before sectioning and staining with hematoxylin and eosin. Liver sections were blindly scored on a scale from 0 to 3 for pigment levels, Kupffer cell density, portal tract inflammation, hemozoin deposition, extramedullary hematopoiesis, sinusoidal leukocyte density, sinusoidal adherence of leukocytes, and presence of microabscesses. Spleen sections were blindly scored on a scale from 0 to 3 for hyperplasia, extramedullary hematopoiesis, pigment, and levels of histiocytes and neutrophils. Pathology scores of control and treated mice were analyzed by unpaired t-test.

ABA Extraction and Quantification.

ABA was extracted from mouse plasma as described (Engelberth, *J Vis Exp*, 2009, 28:1127). Briefly, 50 µL of plasma was added to 200 µL extraction buffer (1-propanol:H2O:concentrated HCL at a 2:1:0.002 volume ratio) and vortexed. 500 µL of ethyl acetate was added and the samples were vortexed again. Samples were spun at 10,000×g for 1 minute and the upper layer collected and dried under a steady stream of air. Dried samples were re-eluted in 100% methanol and ABA levels determined using the Phytodetek Abscisic Acid ELISA kit (Agdia) according to the manufacturer's instructions. ABA levels in the plasma of control and ABA-supplemented mice, 4-5 per group, were analyzed by Mann Whitney test.

ABA was extracted from four independent *P. falciparum* cultures. In brief, infected RBCs (~200 mg) were collected, frozen, quickly weighed, and immediately frozen in liquid nitrogen. Samples were finely ground in mortar while frozen and transferred to a 4 ml screw top Supelco vial containing 1200 µl of 2-propanol/$H_2O$/HCl (2:1:0.002) and sonicated in a water bath for 10 min. Dichloromethane (2 ml) was added to each sample and re-sonicated for 10 min. The bottom dichloromethane/2-propanol layer was then transferred to a 4 ml glass vial, evaporated under a constant air stream and the resultant pellet was subsequently dissolved in 300 µl of diethyl ether/methanol (9:1, vol/vol) followed by the addition of 9 µl of a 2.0 M solution of trimethylsilyldiazomethane in hexane in order to convert the carboxylic acids into the methyl esters. During this step ABA is converted to MeABA. The vials were capped, vortexed, and incubated at room temperature for 25 min. Then 9 µl of 12% acetic acid in hexane were added to each sample and left at room temperature for another 25 min in order to destroy all excess trimethylsilyldiazomethane.

The resulting methyl ester volatiles were captured on Super-Q (Alltech Inc., State College, Pa.) columns by vapor-phase extraction. The trapped metabolites were then eluted with 150 µl of dichloromethane and analyzed by GC-MS using a Hewlett and Packard 6890 series gas chromatograph coupled to an Agilent Technologies 5973 network mass selective detector operated in electronic ionization (EI) mode. One µl of the sample was injected in splitless mode at 250° C. and separated using an HP-5MS column (30 m×0.25 mm, 0.25 µm film thickness) held at 40° C. for 1 min after injection, and then at increasing temperatures programmed to ramp at 15° C./min to 250° C. (10 min), with helium as the carrier gas (constant flow rate 1.0 ml/min). Measurements were carried out in selected ion monitoring (SIM) 190 m/z for MeABA and 194 m/z for MeDtABA (D6 deuterated standard).

Mosquito Rearing and Infections.

*Anopheles stephensi* Liston (Indian wild-type strain) were reared and maintained at 27° C. and 75% humidity. For all feeding experiments, 3-5-day-old female mosquitoes were maintained on water pads for 24 hours and then allowed to bloodfeed for 30 minutes on control or ABA-supplemented *P. yoelii* 17XNL-infected mice. Cohorts of 50 mosquitoes were allowed to feed on each mouse at 5 days post-infection. Immediately after feeding non-engorged mosquitoes were removed. Ten days post-feeding, midguts were dissected, stained with 0.5% mercurochrome, and oocysts counted by microscopy.

For *P. falciparum* infections *A. stephensi* were fed on a 1:1 ratio of *P. falciparum*-infected RBCs containing a treatment or diluent control and provided in a Hemotek Insect Feeding System (Discovery Workshops). ABA was eluted in 100% ethanol and stored at −20 C for up to 6 months. ABA stock was diluted with PBS and added into blood immediately before feeding for final concentrations of 10 nM and 100 nM. For L-NAME feeds mosquitoes were maintained on sugar cubes and water pads containing 1 mg/mL L-NAME for 72 hours before the feed and throughout the course of infection. Infection prevalence data were analyzed by Fisher's Exact Test. Oocyst intensities were analyzed by Mann-Whitney test.

*P. falciparum* Growth Assays.

*P. falciparum* NF54 cultures were synchronized and aliquots plated in complete RPMI 1640 with HEPES, hypoxanthine, and 10% heat inactivated human serum. Parasites were treated with 10 nM ABA, 100 nM ABA, or a diluent control and incubated at 37° C. for 48 or 96 hours before culture media was replaced with 10% formalin in RPMI 1640. Red blood cells were stained with 10 ug/mL propidium iodide (Sigma-Aldrich) in PBS at room temperature for 1 hour and infected cells counted with FACS Calibur flow cytometer (BD Biosciences). Four replicates were carried out, each using a separate parasite culture passage. Relative changes in growth were normalized to controls set at 1 and analyzed by one-sample t-test.

Studies of the effects of ABA on gametocyte formation were performed with *P. falciparum* 3D7 engineered to express GFP under the control of alpha tubulin II and Pfs25 promoters. Parasite cultures were synchronized using sorbitol. At 48 hours post-synchronization, 200 µL aliquots of parasite culture and complete RPMI medium were placed in a 96-well flat-bottomed plate and treated with 10 nM ABA, 100 nM ABA, or a diluent control. Media and treatments were refreshed every 48 hours. At 4, 6 and 8 days after the start of treatment, separate aliquots were harvested, media was removed, and replaced with 10% formalin for 1 hour at room temperature. Formalin was removed and replaced with PBS before gametocyte levels were measured by flow cytometry using a FACS Calibur flow cytometer (BD Biosciences) with a GFP filter. Four replicates were carried out, each using a separate parasite culture passage. Relative changes in gametocyte numbers were normalized to controls set at 1 and analyzed by one-sample t-test.

Gene Expression.

For mosquito immune gene expression, 20 midguts were dissected from mosquitoes in each treatment group at 1, 2, 4, 6, 8 and 24 hours post-feeding. Midguts were sonicated and stored in Trizol at −20° C. for up to a week before RNA was extracted according to manufacturer's instructions. cDNA synthesis was carried out using QantiTect Reverse Transcription Kit (Qiagen) and 200 ng of cDNA used per reaction for qRT-PCR with Sybr Green (Applied Biosystems). Fold changes in expression levels were calculated using the comparative threshold cycle method. Data were normalized to the housekeeping gene ribosomal protein S7 and to the control treatment. Primers and cycling conditions for AsNOS, defensin, LRIM, TEP1, and APL1 were as previously described (Hauck E S, et al. *Microbes Infect.* 2013; 15:775-87). For gene expression analysis of mouse liver and spleen, organs were flash frozen after necropsy and stored at −80° C. before RNA was extracted in Trizol and cDNA synthesized. Real-time PCR was performed using TaqMan probe-based expression assays for mouse NOS2, PPARγ (Mm00440940), and β-actin (Applied Biosystems) with volumes and cycling conditions as previously described (Chau et al., *Infect Immun*, 2013, 81:3515-26). Samples were analyzed in triplicate with 250 ng of cDNA per reaction to confirm uniformity of amplification. Data were normalized to β-actin and control-treated mouse mRNA levels. All expression data were analyzed by one sample t-test.

Figure 1A:
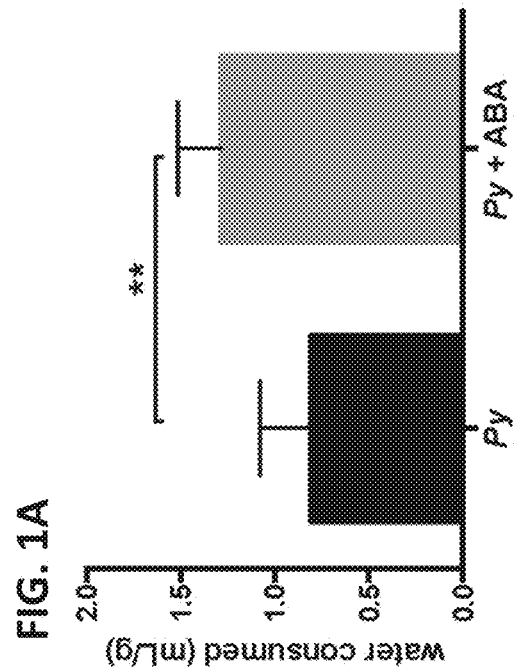
Figure 2C:
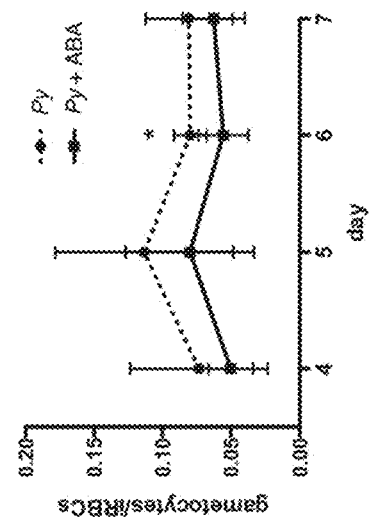
FIG. 2A-C depict the effect of ABA supplementation on *P. yoelii* infection. ABA in plasma is shown in FIG. 2A, parasitemia in ABA-supplemented mice relative to controls is shown in FIG. 2B, and gametocytemia in ABA-supplemented mice is depicted in FIG. 2C.

Example 1: ABA Supplementation Increased Circulating ABA Levels and Decreased Parasitemia and Disease Pathology in P. yoelii-Infected Mice The water of female CD1 mice was supplemented throughout the course of infection with 2.56 mM ABA, equivalent to 100 mg/kg. Infected ABA-supplemented mice consistently drank more water than controls when water consumption was normalized to account for differences in mouse weight (FIG. 1A). Among infected mice, daily weight change was not different over the course of infection, although the average weight of control mice began to drop on day 7 while that of ABA-supplemented mice did not (FIG. 1B). P. yoelii infection had no effect on ABA levels present in mouse plasma (FIG. 2A). In the absence of infection, oral ABA supplementation did not alter ABA levels. However, in the context of P. yoelii infection ABA supplementation increased levels of ABA in plasma over 6-fold compared to non-supplemented infected mice (FIG. 2A). Within control and treatment groups, ABA levels were not correlated with parasitemia.

Figure 2B:
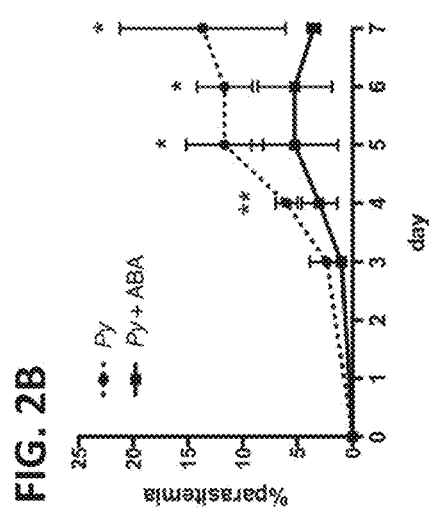
Figure 2A:
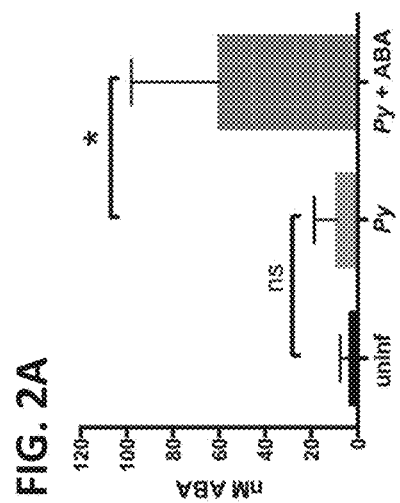

Parasitemia was reduced in ABA-supplemented mice relative to controls starting on day 4 post-infection and continuing until necropsy on day 7 (FIG. 2B). ABA-supplemented mice were also less lethargic at necropsy compared to controls. In addition to decreased parasitemia, ABA-supplemented mice exhibited reduced gametocytemia, which was different relative to controls on day 6 of infection (FIG. 2C).

Figure 4A:
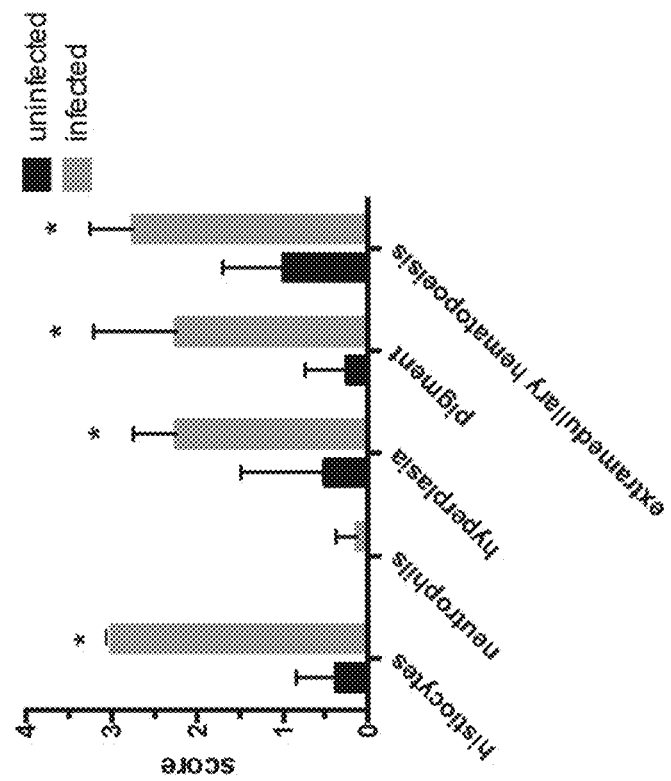
FIG. 4A-B depict hemozoin deposition, pigment, portal tract inflammation, extramedullary hematopoeisis, Kupffer cell density in the liver (FIG. 4A) and histiocyte density, pigment deposition, and extramedullary hematopoiesis in the spleen (FIG. 4B) for *P. yoelii*-infected and control mice.

To define the histologic effects of ABA treatment and the ABA-dependent decrease in parasitemia in tissues relevant to infection, livers and spleens were scored and compared among supplemented and control mice in the presence and absence of parasite infection. In the absence of infection, ABA treatment decreased the number of sinusoidal leukocytes in the liver; this trend was also evident in P. yoelii-infected mice (FIG. 3A). In P. yoelii-infected mice, hemozoin deposition, pigment, portal tract inflammation, extramedullary hematopoeisis, and Kupffer cell density were increased relative to controls (FIG. 4A), but these levels were not altered by ABA treatment. In addition, the livers of ABA-treated infected mice had fewer adhered leukocytes (FIG. 3B) and fewer microabscesses than control mice on day 7 post-infection (FIG. 3C).

Figure 4B:
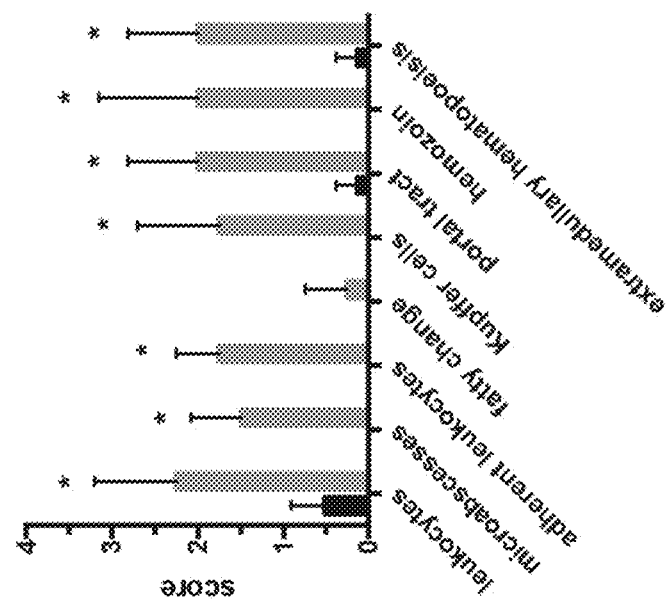
Figure 5:
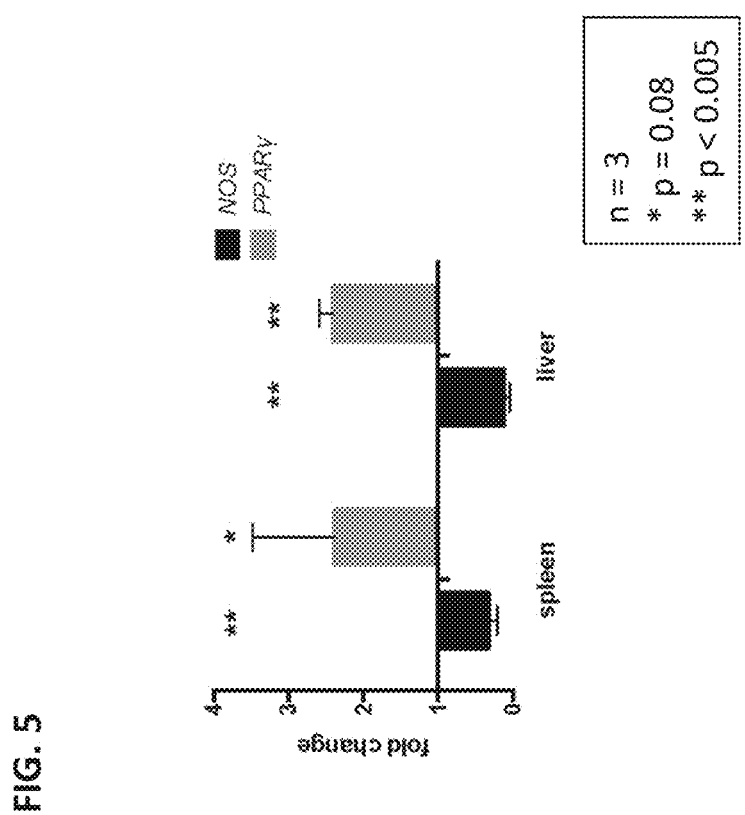
FIG. 5 depicts liver and spleen transcript levels of nitric oxide synthase (NOS) and peroxisome proliferator activated receptor gamma (PPARγ).

In P. yoelii-infected mice, histiocyte density, pigment deposition, and extramedullary hematopoiesis in the spleen were increased relative to control mice (FIG. 4B), but these changes were not altered by ABA treatment. However, lymphoid hyperplasia of the spleen was increased in infected mice and this reduced by ABA treatment (FIG. 3D). Consistent with this ABA-dependent reduction in inflammatory pathology, there were decreased transcript levels of nitric oxide synthase (NOS) and increased transcript levels of the anti-inflammatory regulator peroxisome proliferator activated receptor gamma (PPARγ), which are regulated by ABA in both the liver and spleen (FIG. 5).

Figure 6B:
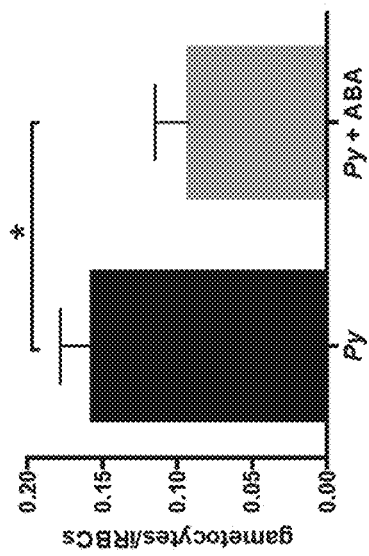
FIG. 6A-D depict the effect of ABA supplementation on *P. yoelii* transmission. Parasitemia and gametocytemia of ABA-supplemented mice are depicted in FIG. 6A and FIG. 6B, respectively. The prevalence of infected mosquitoes that fed on control mice compared to infection prevalence of mosquitoes that fed on ABA-supplemented mice is shown in FIG. 6C and FIG. 6D.
Figure 6D:
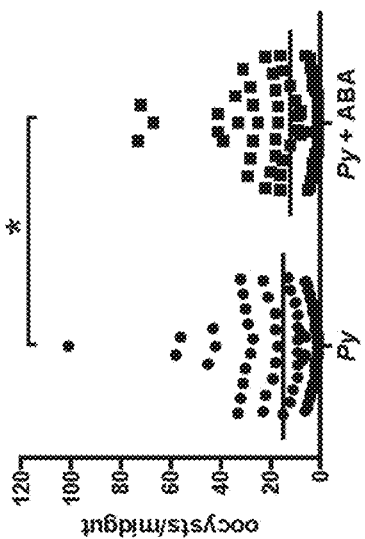
Figure 6A:
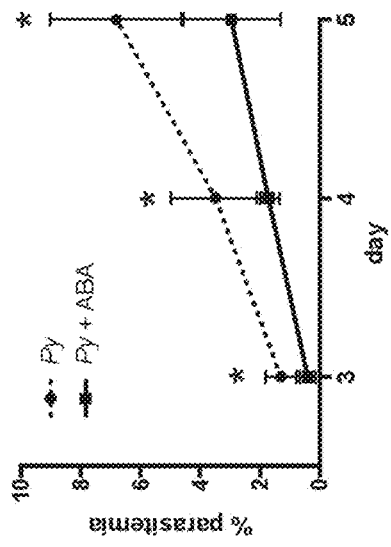
Figure 6C:
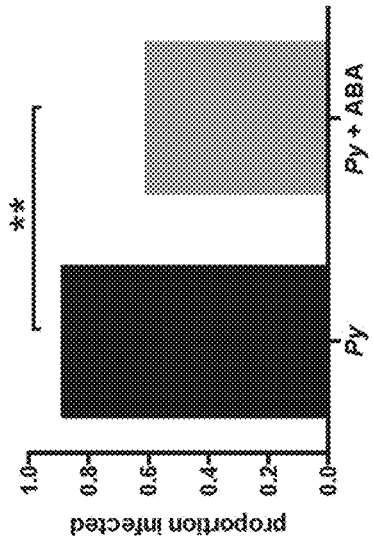

Example 2: ABA Supplementation of Mice Reduced P. yoelii Transmission to Mosquitoes ABA-supplemented mice showed reduced parasitemia compared to controls starting on day 3 and reduced gametocytemia on day 5 post-infection, near peak gametocytemia (FIG. 6A-6B). On day 5, each mouse in the ABA-supplemented and control groups was exposed to 50 female A. stephensi. Ten days later mosquito midguts were dissected and oocysts counted to measure mosquito infection prevalence and intensity. The prevalence of infected mosquitoes that fed on control mice was 88.8% (mean of 15 oocysts per midgut) compared to an infection prevalence of 60.9% of mosquitoes that fed on ABA-supplemented mice (mean of 12 oocysts per midgut) (FIG. 6C-6D). The 31.4% reduction in prevalence is notable and, given that a single oocyst can produce sufficient sporozoites for transmission to a human host, is a more relevant measure for malaria control.

Example 3: ABA does not Alter P. falciparum Growth and Gametocyte Development In Vitro Cultures of P. falciparum were treated with 10 nM ABA, 100 nM ABA, or diluent control to assess the effects of ABA on parasite development. At 48 and 96 hours after treatment, ABA had no effect on asexual growth relative to untreated control cultures (FIG. 7A). In addition, treatment with ABA had no effect relative to controls on gametocyte levels at 6, 8 or 10 days post culture synchronization, when gametocytogenesis is initiated (FIG. 7B). Thus, ABA-dependent decreases in parasitemia and gametocytemia in the mouse and decreased transmission to mosquitoes were not caused by a direct effects of ABA on the parasites but rather the effects of ABA were due to indirect effects on mouse, and mosquito, physiology.

Figure 8A:
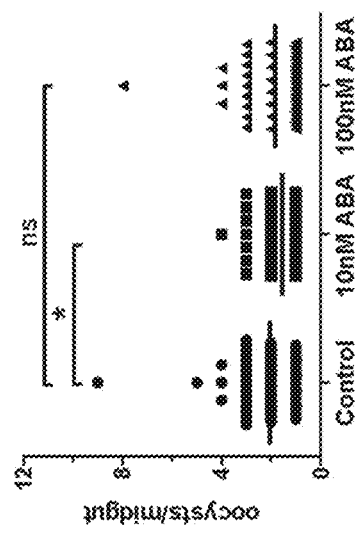
FIG. 8A-D depict the effect of ABA on *P. falciparum* transmission.
Figure 8B:
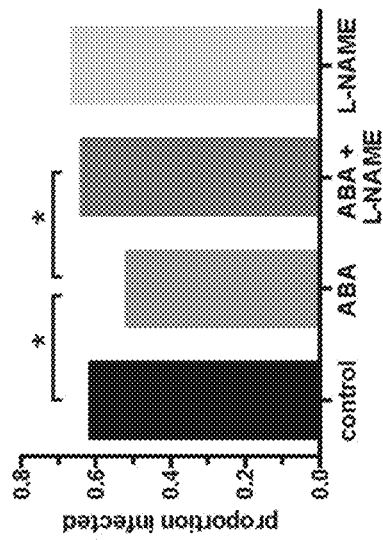

Example 4: Supplementation of ABA in a P. falciparum-Infected Bloodmeal Reduced Transmission to A. stephensi by Increasing NO Production in the Mosquito Midgut Gametocyte cultures of P. falciparum were supplemented with 10 nM ABA, 100 nM ABA, or an equivalent volume of diluent as a control immediately prior to feeding to A. stephensi. Mosquitoes were dissected at 10 days after feeding to record infection prevalence and intensity. Supplementation with 10 nM or 100 nM ABA reduced infection prevalence in A. stephensi by 30% and 36%, respectively, relative to control (FIG. 8A). Notably, these reductions were consistent with the reduction in the prevalence of infected mosquitoes fed on ABA-supplemented, P. yoelii-infected mice relative to controls (31.4%, FIG. 6C). Among P. falciparum-infected mosquitoes, mean oocysts per midgut decreased from 2.1 in controls to 1.6 with 10 nM ABA (FIG. 8B).

Transcript levels of a panel of immune genes previously described to play a role in the mosquito immune response to malaria parasites were examined. These included genes encoding the antimicrobial peptide defensin, inducible A. stephensi nitric oxide synthase (AsNOS), and the complement-like proteins LRIM, APL1, and TEP1. Mosquitoes were provided with a P. falciparum-infected bloodmeal supplemented with 100 nM ABA or with an equivalent volume of diluent as control, then analyzed at 1-24 hours post feeding.

Figure 8C:
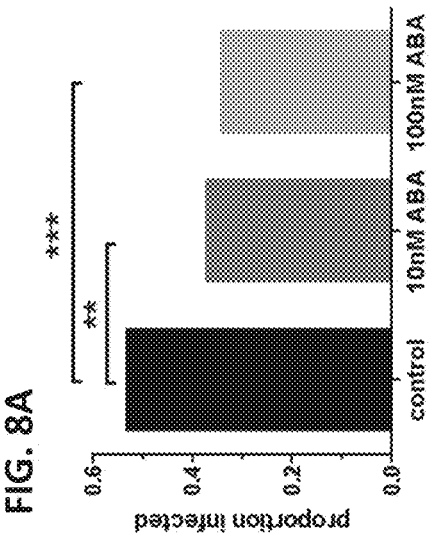
Figure 8D:
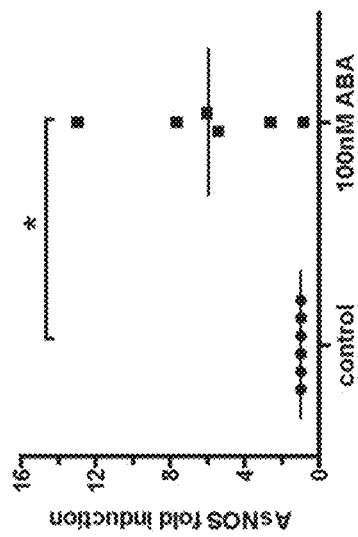
Figure 10:
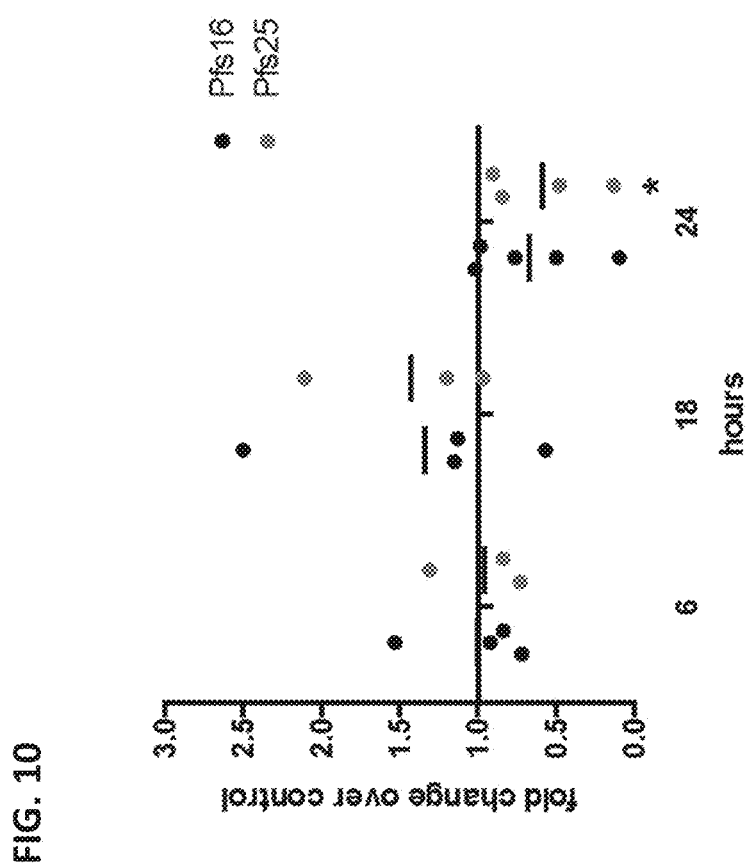
FIG. 10 illustrates that increased parasite death with ABA treatment occurs within the mosquito midgut between 18 and 24 hours post-bloodmeal. Expression levels are shown of *P. falciparum* genes Pfs16 and Pfs25 in ABA-supplemented parasite-fed mosquito midguts. Data are normalized to mosquito and parasite ribosomal genes s7 and A18s. Each dot represents one replicate of 10 pooled midguts. Data are shown as fold change relative to control and were analyzed by one sample t-test. * p<0.05.
Figure 12A:
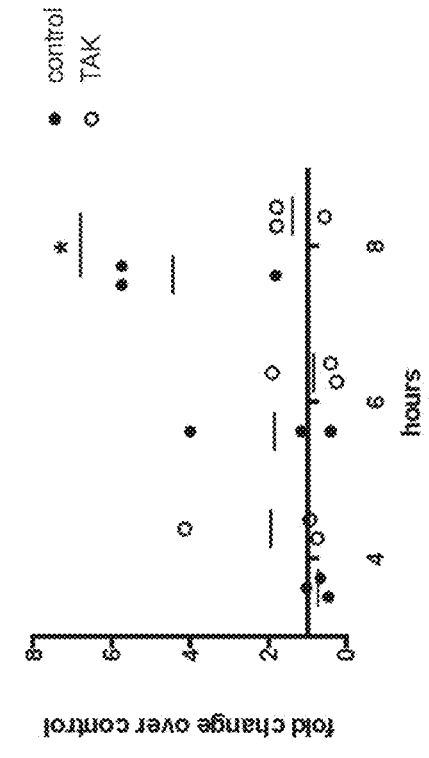
FIG. 12A-D illustrate that knocking down TAK reduces the transcription of NF-κB-regulated immune genes in response to ABA. Fold change is shown in expression levels of APL1 (FIG. 12A), LRIM (FIG. 12B), TEP (FIG. 12C), and Defensin (FIG. 12D) in ABA-supplemented *P. falciparum*-fed mosquitoes fed either a control- or TAK-morpholino. Each dot represents one replicate of 10 pooled midguts. Data were normalized to their respective morpholino controls. Data were analyzed by one-sided t-test. * $p<0.05$.
Figure 12C:
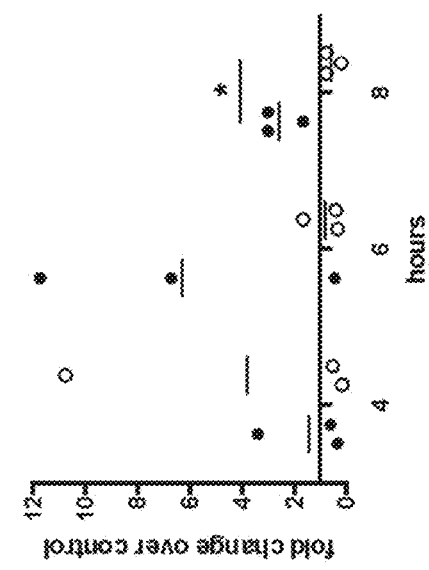
Figure 12B:
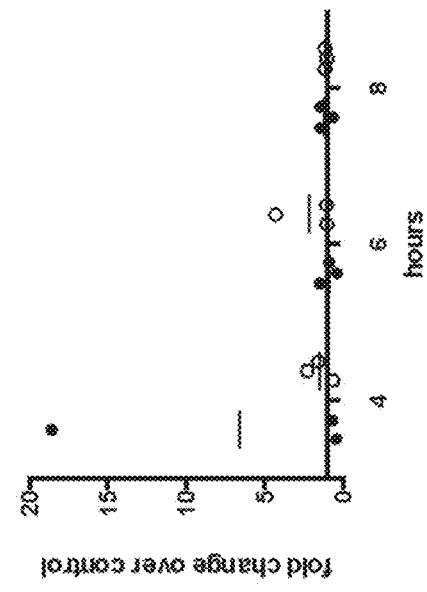
Figure 12D:
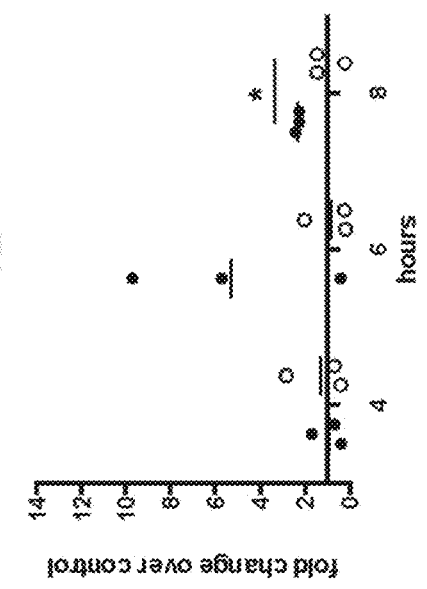
Figure 13A:
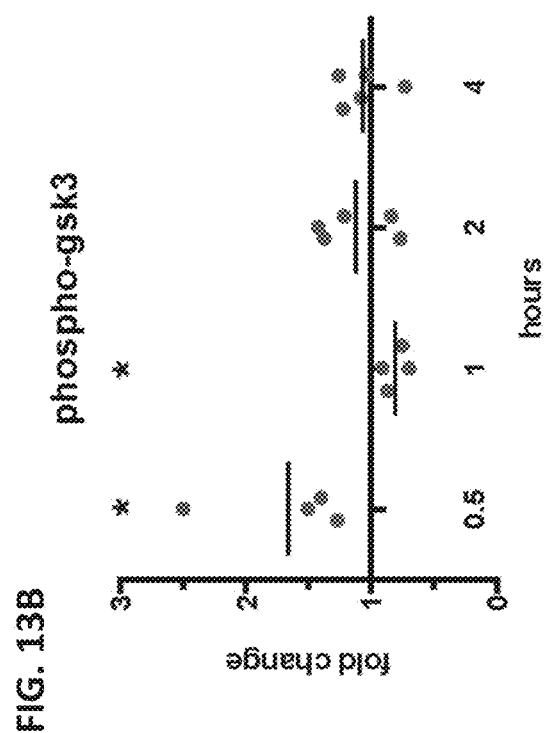
FIG. 13A-B illustrate that ABA alters phosphorylation of AMPK and gsk3 in the midgut. Fold change is shown in levels of phosphorylated AMPK (FIG. 13A), and gsk3 (FIG. 13B) in the midguts of ABA-treated, *P. falciparum*-fed mosquitoes compared to controls. Each dot represents one replicate of 15 pooled midguts. Data were analyzed by one sample t-test. * $p<0.05$. However, ABA does not alter MAPK phosphorylation in the midgut. Specifically, phospho-erk, phospho-jnk and phospho-p38 levels in the midgut did not differ significantly from 0 to 4 hours (data not shown).
Figure 13B:
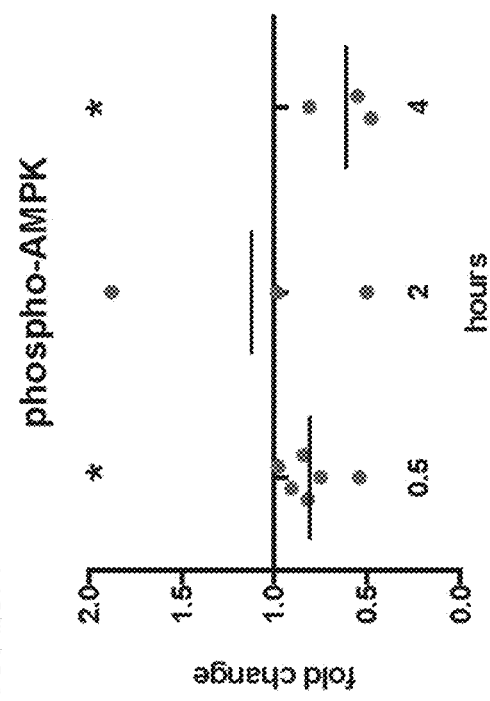
Figure 14A:
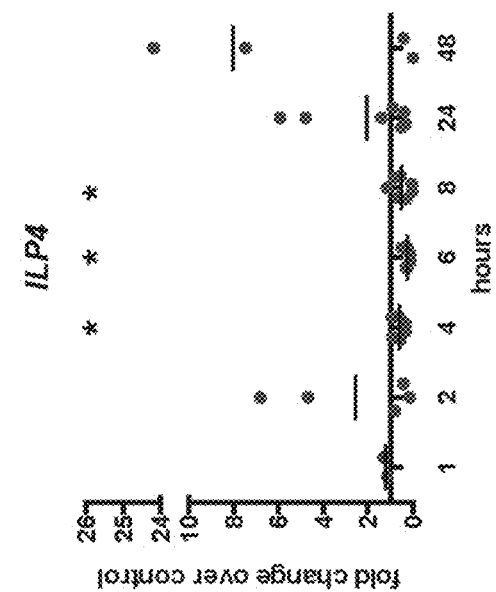
FIG. 14A-B illustrate that ABA reduces insulin-like peptide expression in the midgut. Specifically, mRNA levels are shown of ILP3 (FIG. 14A) and ILP4 (FIG. 14B) in ABA-treated, *P. falciparum*-fed mosquito midguts. Data are shown as fold change compared to control-treated mosquitoes. Each dot represents one replicate of 10 pooled midguts. Data were analyzed by one sample t-test. * $p<0.05$.
Figure 14B:
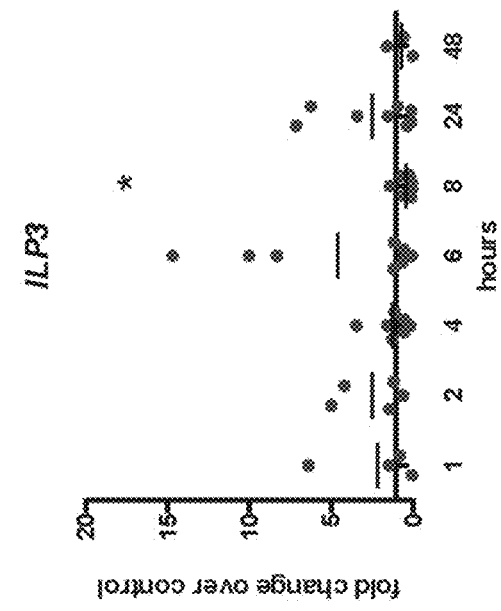
Figure 15A:
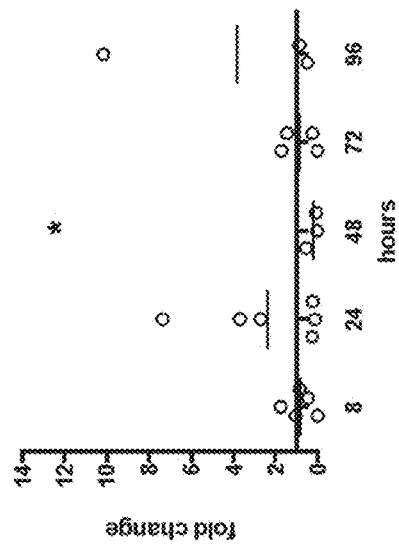
FIG. 15A-D illustrate that ABA reduces expression of genes involved in midgut epithelial cell turnover. mRNA levels are shown of prospero (FIG. 15A), escargot (FIG. 15B), ATG6 (FIG. 15C), and ATG8 (FIG. 15D) in ABA-treated *P. falciparum*-fed mosquito midguts. Data are shown as fold changed compared to control-treated mosquitoes. Each dot represents one replicate of 10 pooled midguts. Data were analyzed by one sample t-test. * $p<0.05$. nd indicates the prospero was not detectable at 72 or 96 hours.
Figure 15C:
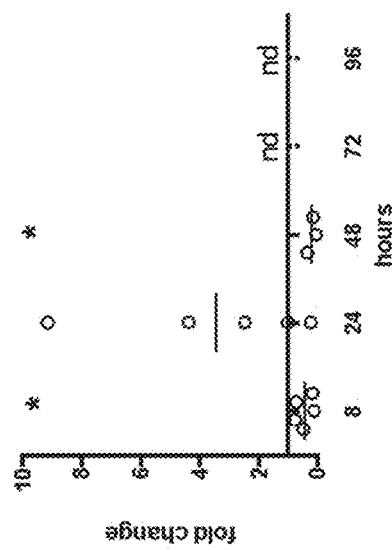
Figure 15B:
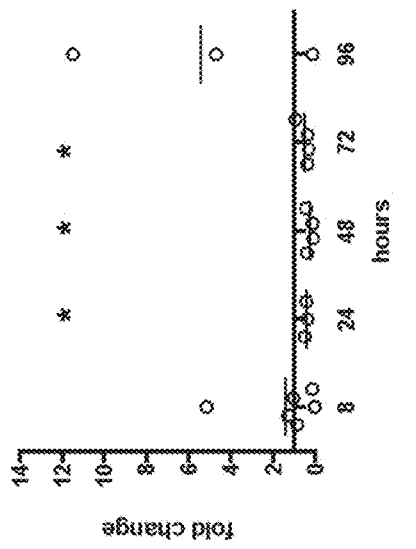
Figure 15D:
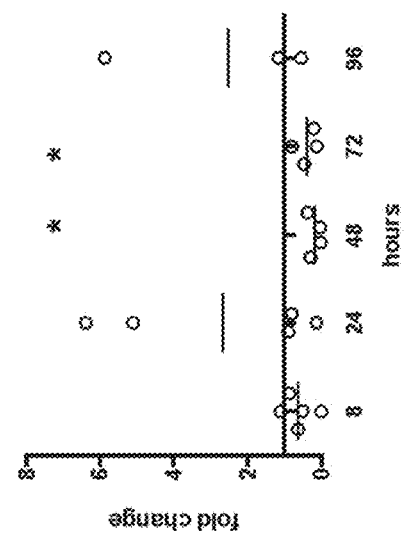
Figure 16:
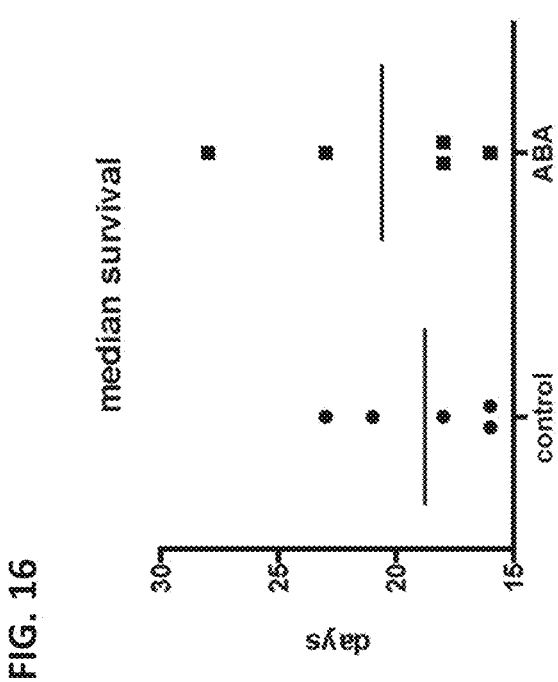
FIG. 16 illustrates that ABA supplementation does not alter mosquito median survival. Median survival of control and ABA-treated mosquitoes from five lifespans in which mosquitoes received a weekly control or ABA-supplemented uninfected bloodmeal. Each lifespan was conducted with 300 female mosquitoes per treatment. Data were analyzed by Wilcoxon matched-pairs signed rank test.
Figure 17B:
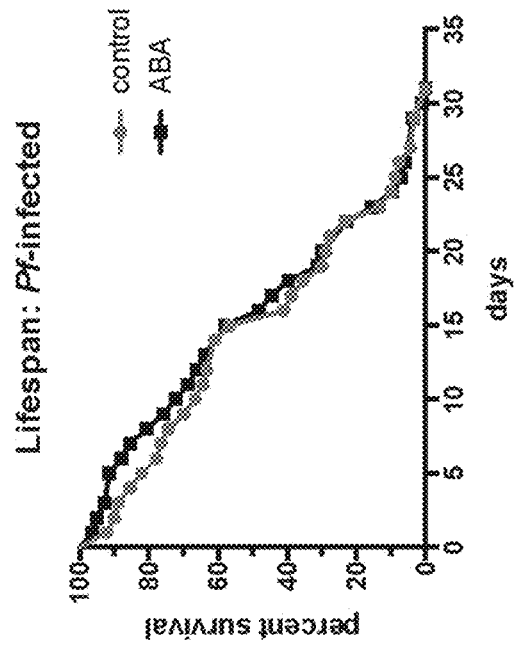
FIG. 17A-B illustrate that ABA supplementation does not alter lifespan in the context of nutrient stress or *Plasmodium* infection.
Figure 17A:
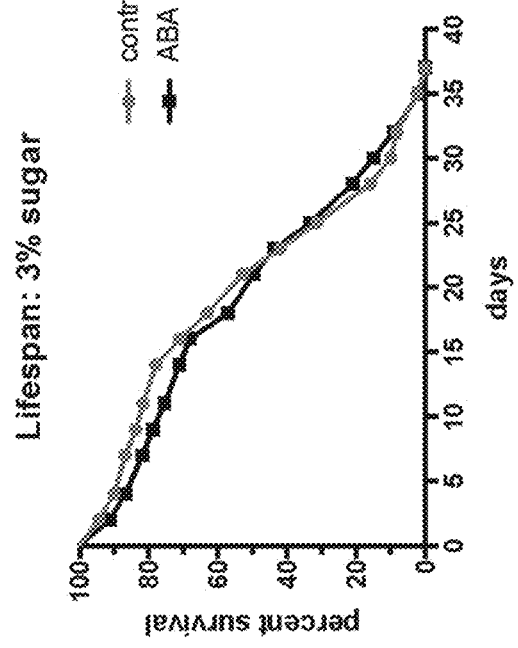
Figure 19A:
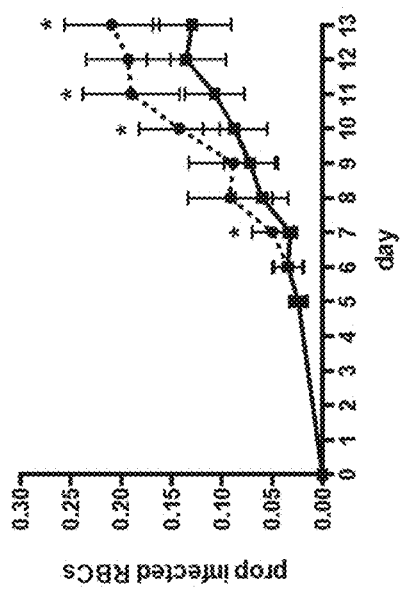
FIG. 19A-C illustrate that ABA supplementation significantly reduces parasitemia in C57Bl/6 mice infected with *P. yoelii* 17XNL. Daily parasitemia of three separate cohorts of mice with and without ABA supplementation. 3 to 5 mice were used per treatment in each infection. Data were analyzed by one-sided, unpaired t-test. # $p<0.1$, * $p<0.05$, ** $p<0.005$.
Figure 19B:
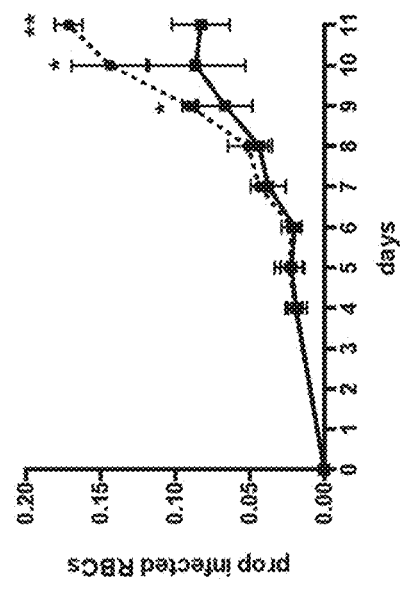
Figure 19C:
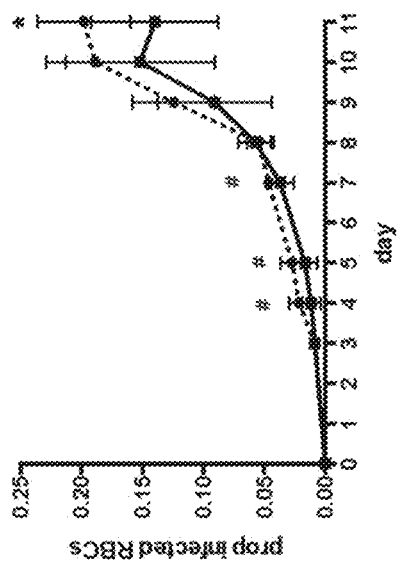
Figure 20A:
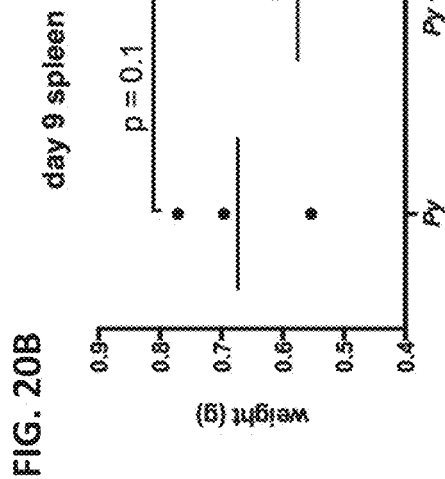
FIG. 20A-C illustrate that ABA supplemented mice have reduced hepatosplenomegaly and evidence of improved liver function. Shown are weights of whole liver (FIG. 20A) and spleen (FIG. 20B) from control and ABA-supplemented mice on day 9 post-infection with *P. yoelii* 17XNL. Also shown are blood urea nitrogen levels (FIG. 20C) in plasma of uninfected and *P. yoelii*-infected, control and ABA-supplemented mice on day 11 post-infection. Data were analyzed by unpaired t-test.
Figure 20B:
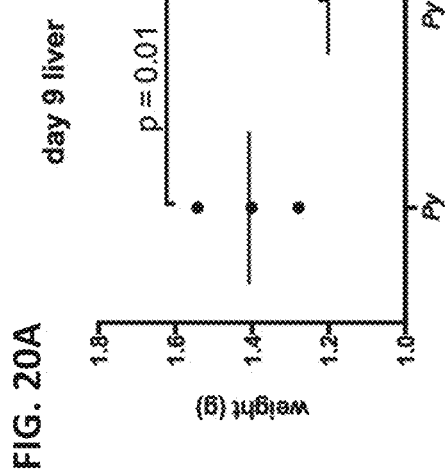
Figure 20C:
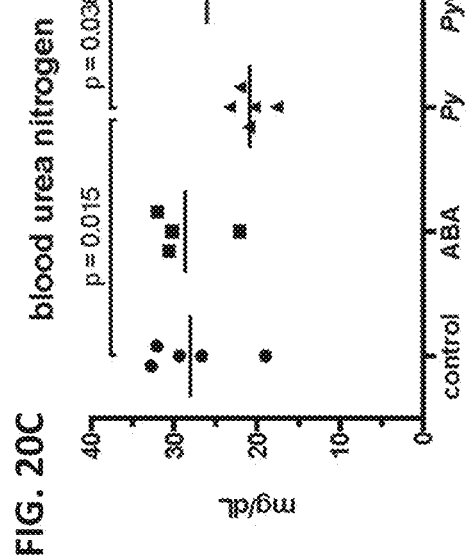
Figure 21B:
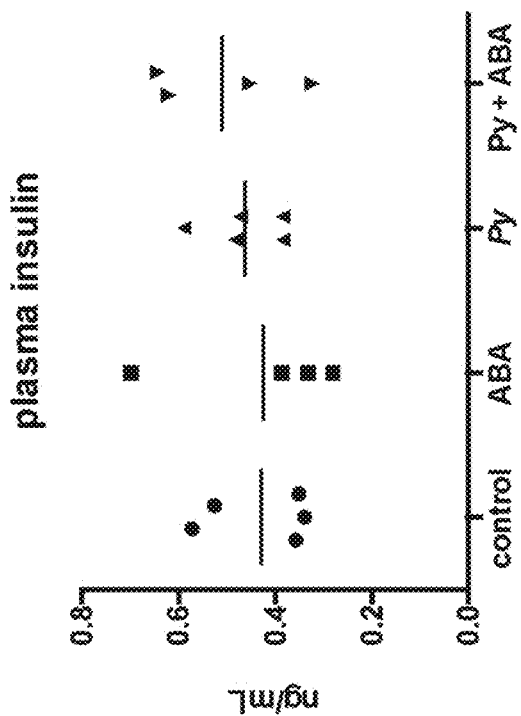
FIG. 21A-B illustrate that ABA supplementation does not alter glucose or insulin levels in mouse plasma. Shown are glucose (FIG. 21A) and insulin (FIG. 21B) levels present plasma of uninfected and *P. yoelii*-infected, control and ABA-supplemented mice on day 11 post-infection.
Figure 21A:
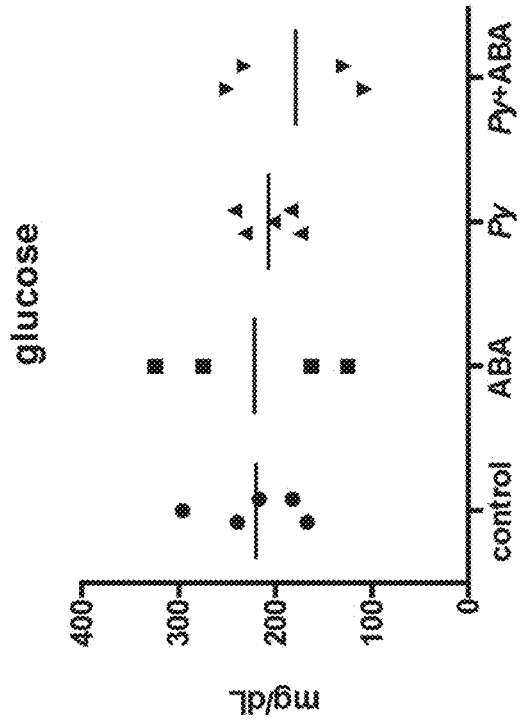
Figure 22A:
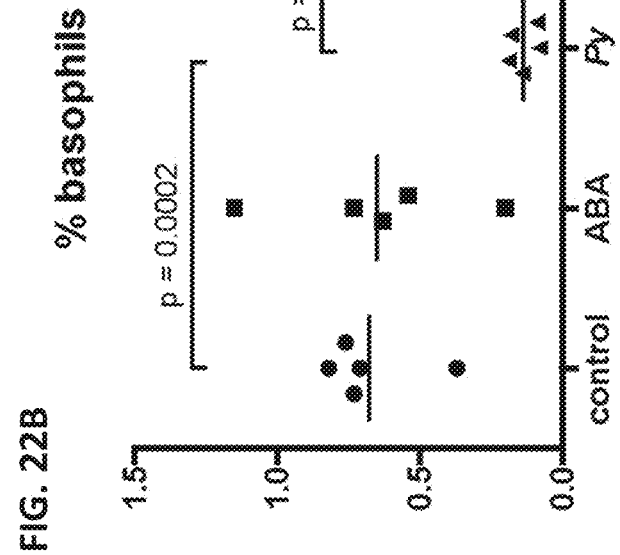
FIG. 22A-B illustrate that ABA supplementation partially rescues decrease in eosinophils and basophils seen with *P. yoelii* infection. Shown are the percentage of eosinophils (FIG. 22A) and basophils (FIG. 22B) present in whole blood of uninfected and *P. yoelii*-infected, control and ABA supplemented mice on day 11 post-infection. Data were analyzed by unpaired t-test.
Figure 22B:
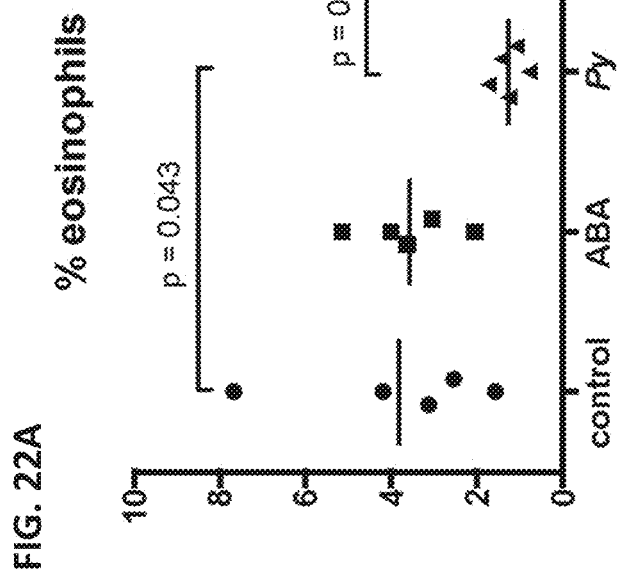
Figure 23A:
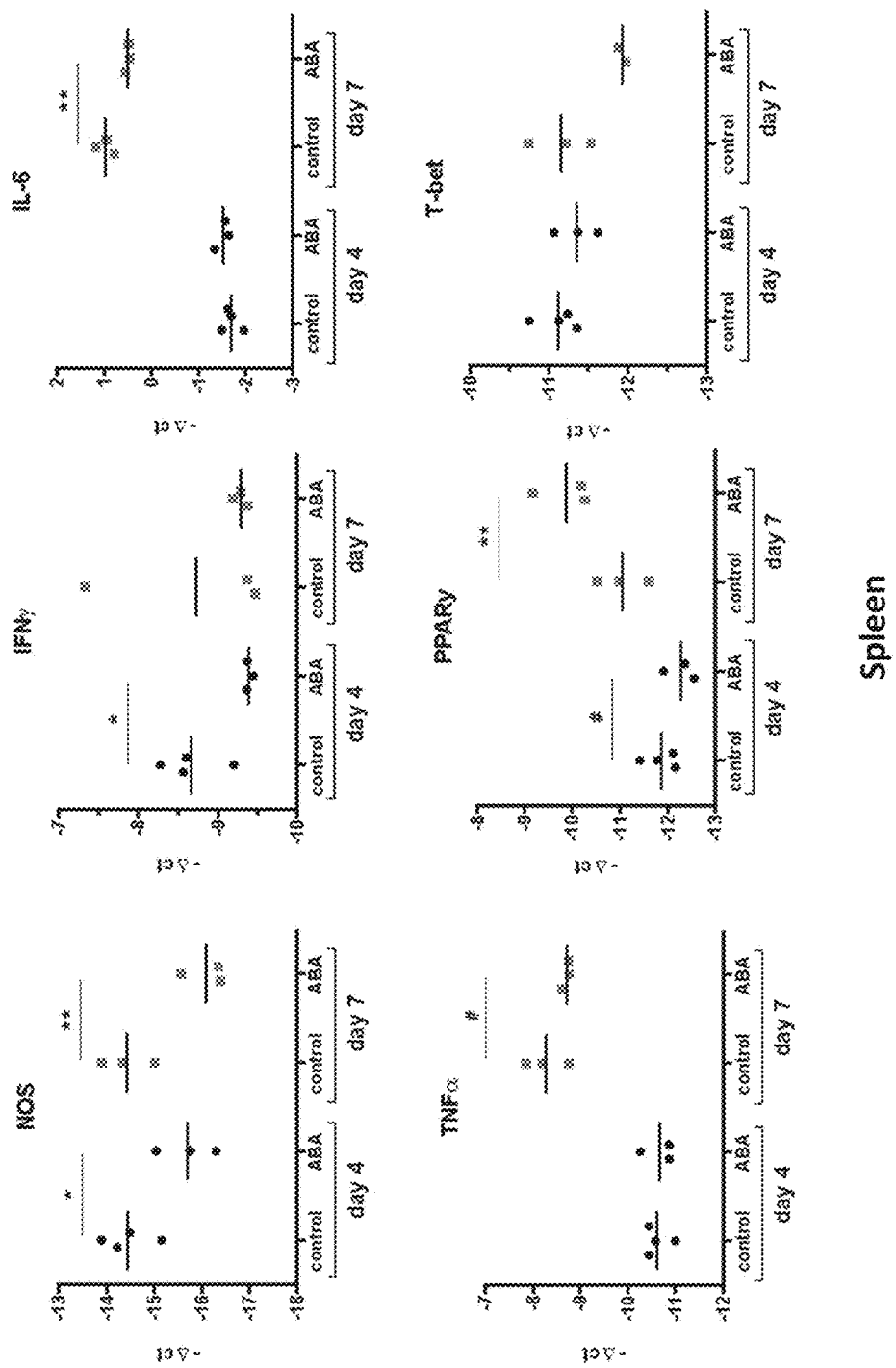
FIG. 23A-B illustrate that ABA supplementation alters cytokine expression in the spleen and liver of infected mice consistent with enhanced IgG production and inflammasome activation. Shown are mRNA levels of cytokine and immune-regulators in the spleen (FIG. 23A) and liver (FIG. 23B) of control and ABA-supplemented CD1 mice on day 4 and 7 post-infection with *P. yoelii* 17XNL. Data are shown as $-\Delta ct$, normalized to $\beta$-actin and were analyzed by unpaired t-test. # $p<0.1$ * $p<0.05$ ** $p<0.01$.
Figure 23B:
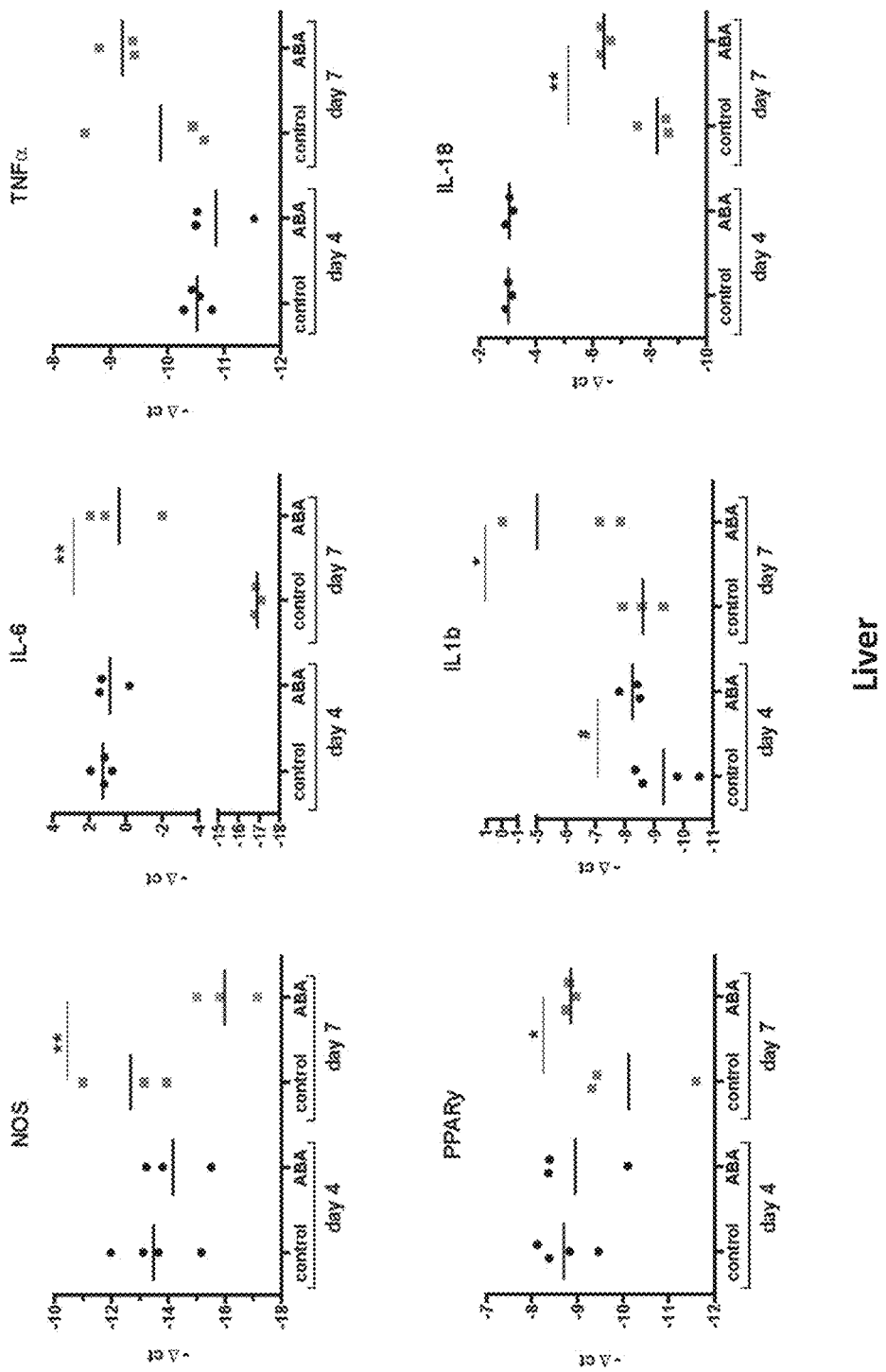
Figure 24:
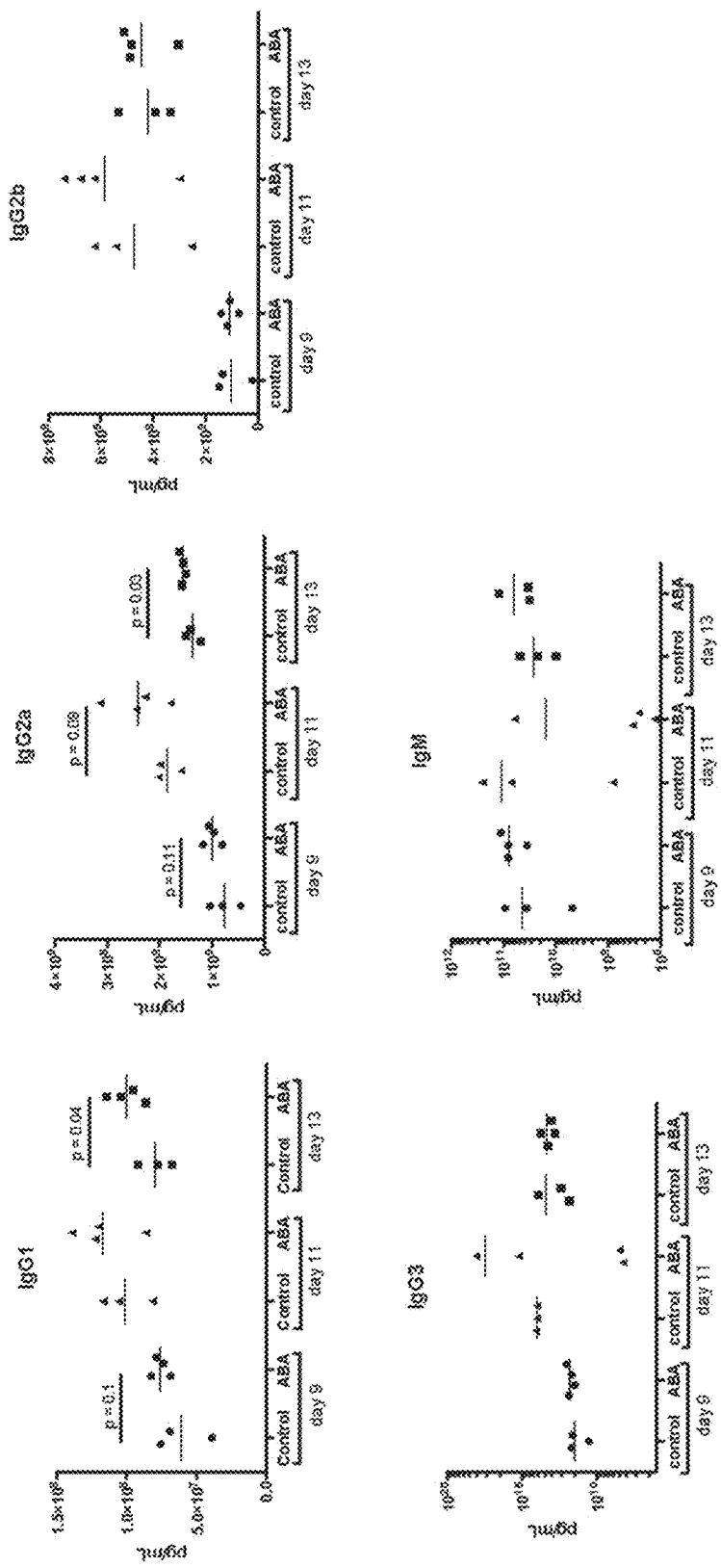
FIG. 24 illustrates that ABA supplementation increases levels of IgG1 and IgG2a in plasma. Concentrations are shown of IgM and IgG antibody isotypes in mouse plasma with and without ABA supplementation on days 9, 11 and 13 post-infection with *P. yoelii* 17XNL. Data were analyzed by unpaired t-test.
Figure 25B:
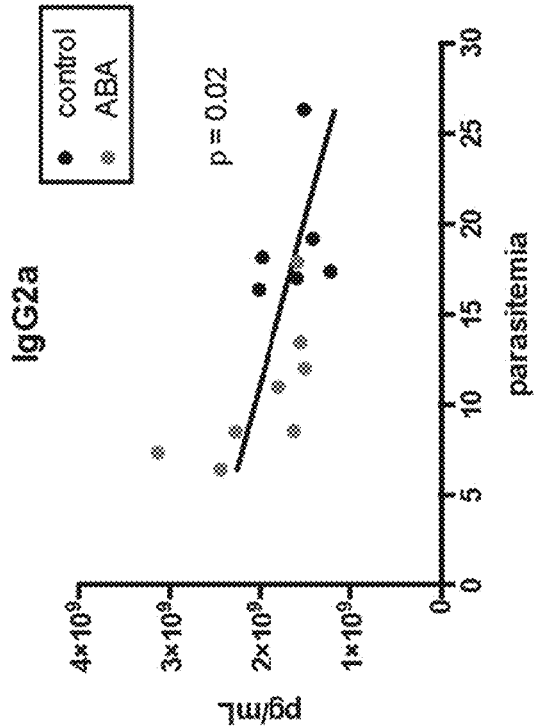
FIG. 25A-B illustrate that the levels of IgG1 and IgG2a negatively correlate with parasitemia. IgG1 (FIG. 25A) and IgG2a (FIG. 25B) levels are plotted against parasitemia of day 11 and 13 control and ABA-treated *P. yoelii*-infected mice. Data were analyzed by linear regression.
Figure 25A:
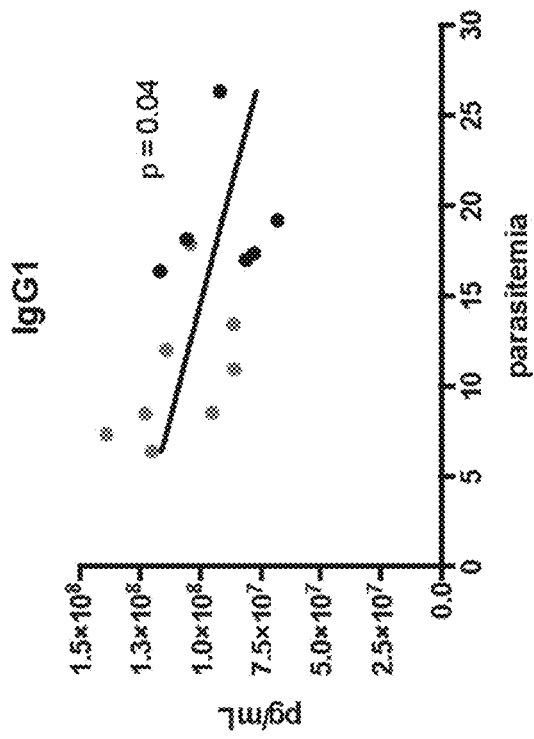
Figure 26A:
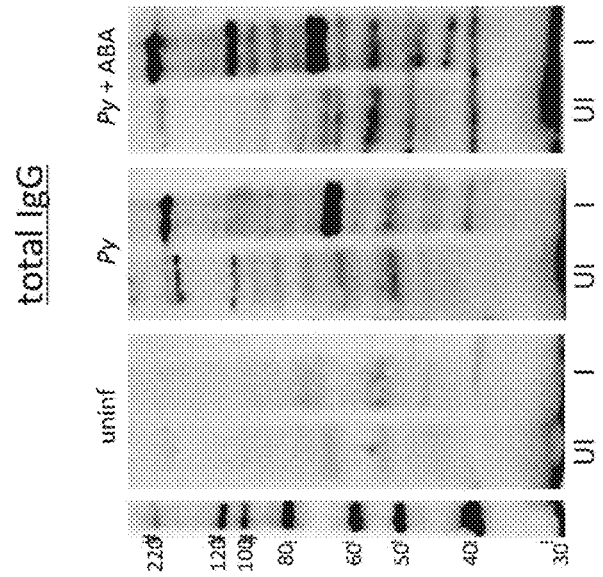
FIG. 26A-C illustrate that ABA-supplementation increased levels of parasite-specific IgG and IgG1 in mouse plasma. Shown are western blots of protein from uninfected and *P. yoelii*-infected RBCs probed with plasma from uninfected, *P. yoelii*-infected, ABA-supplemented *P. yoelii*-infected mice followed by IgG1 (FIG. 26A) and total IgG (FIG. 26B) secondary antibodies. Also shown is a densitometry analysis (FIG. 26C) of IgG1- and total IgG-bound protein from infected RBCs. Data are shown as fold change between control *P. yoelii* and ABA-supplemented *P. yoelii* plasma.
Figure 26B:
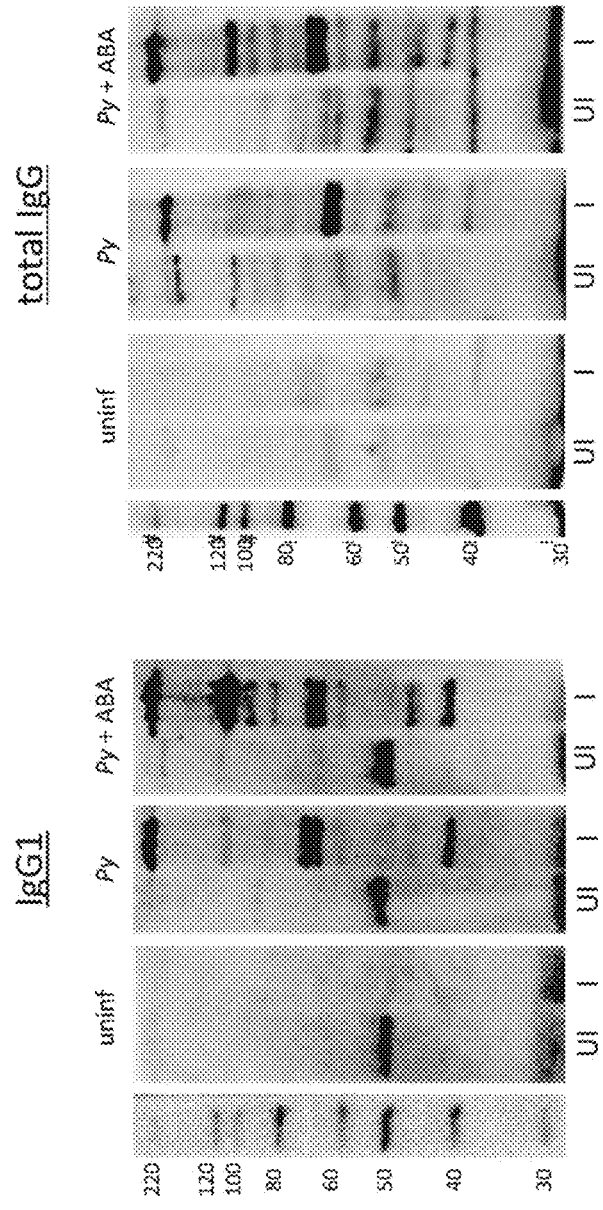
Figure 26C:
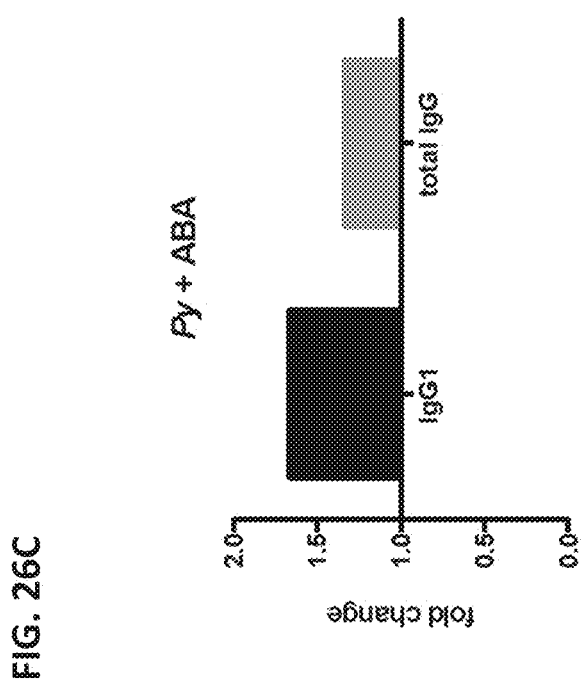
Figure 27B:
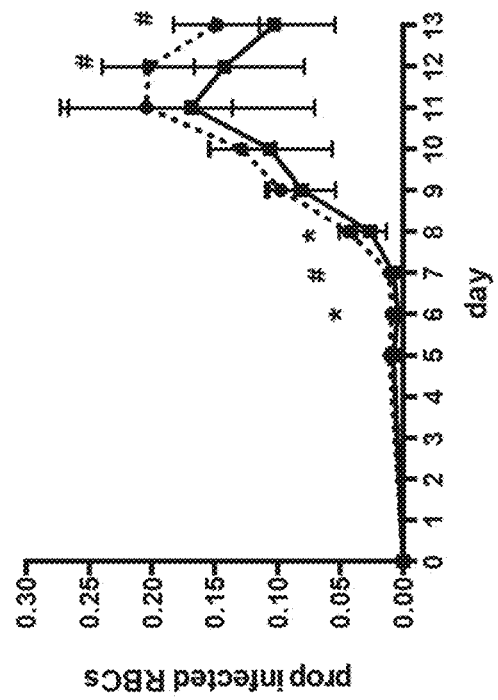
FIG. 27A-B illustrate that plasma from ABA-supplemented mice is partially protective against *P. yoelii* infection.
Figure 27A:
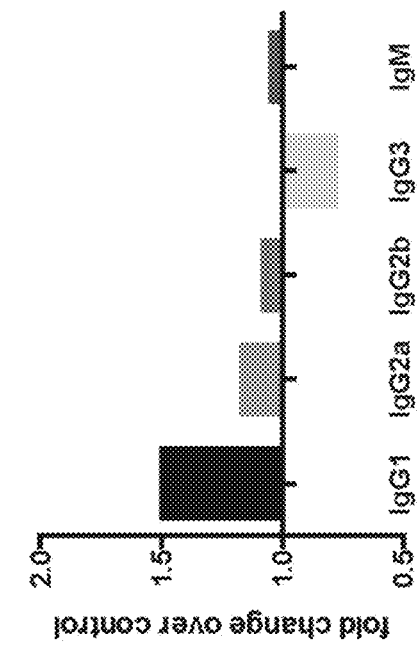
Figure 28A:
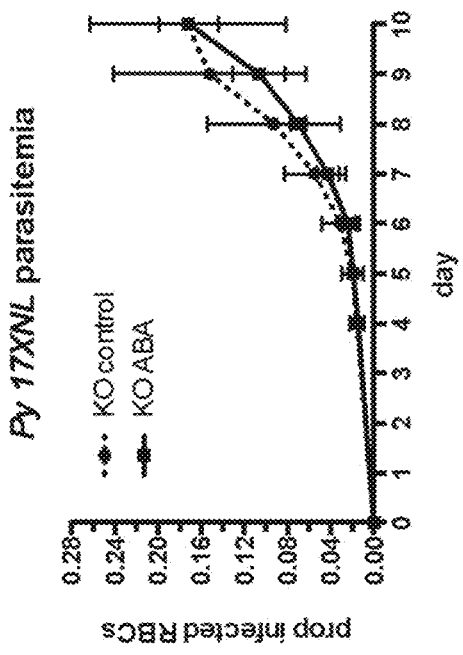
FIG. 28A-B illustrate that ABA has no effect on parasitemia in caspase-1 knockout mice.
Figure 28B:
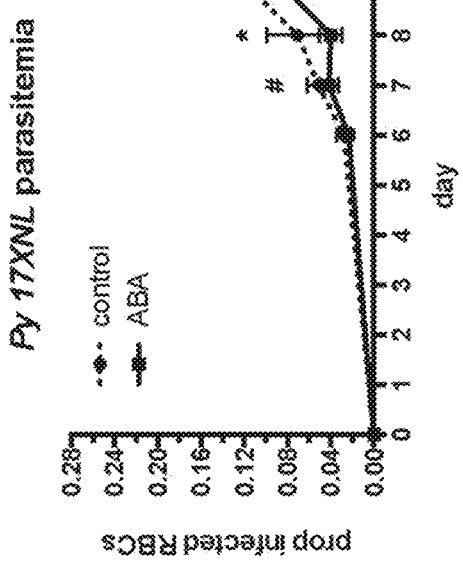

ABA treatment led to an increase in defensin mRNA levels at 4 hours (FIG. 9A) and increased in APL1 expression at 4 and 8 hours post-feeding (FIG. 9C). AsNOS transcript levels were induced up to 13-fold in the midguts of ABA-treated mosquitoes relative to controls between 4-6 hours post-feeding (FIG. 8C). P. falciparum-infected bloodmeals were provided to A. stephensi with 100 nM ABA, with ABA and 1 mg/ml NOS inhibitor Nω-Nitro-L-arginine methyl ester (L-NAME), the inhibitor alone, or with an equivalent volume of ABA and inhibitor diluents as a control. Addition of L-NAME to an ABA-supplemented infected bloodmeal rescued P. falciparum infection prevalence back to control levels while the inhibitor alone had no effect on infection (FIG. 8D).

Example 5: ABA Supplementation Induces a Transient Metabolic Shift that Enhances NF-κB Signaling in the Midgut of *Anopheles stephensi* without Reducing Lifespan or Fecundity ABA is naturally present in human blood and circulating levels can be increased by oral supplementation. As described herein, ABA supplementation in a mouse model of malaria enhances both the mammalian and mosquito immune response to reduce *Plasmodium* infection and transmission. This example demonstrates that ABA reduces *Plasmodium falciparum* infection in the malaria vector *Anopheles stephensi* by increasing phosphorylation of TGF-β-activated kinase (TAK), releasing inhibition of NF-κB, and increasing expression of NF-κB-regulated immune genes. Additional ABA-induced changes in gene expression and protein phosphorylation are indicative of a transient metabolic shift that enhances NF-κB activity without significantly effecting mosquito lifespan or fecundity.

FIG. 10 through FIG. 18A-C and Table 5-1 support the use of ABA for reducing transmission of *Plasmodium* by mosquitos.

TABLE 5-1

ABA supplementation does not alter mosquito lifespan[#]

| Replicate | Median Survival (days) ABA | Median Survival (days) Control | P value Log-rank test | P value Gehan-Breslow-Wilcoxon test |
|---|---|---|---|---|
| 1 | 21 | 28 | <0.0001 | <0.0001 |
| 2 | 16 | 18 | 0.0012 | 0.054 |
| 3 | 18 | 18 | 0.531 | 0.425 |
| 4 | 23 | 23 | 0.231 | 0.288 |
| 5 | 16 | 16 | 0.093 | 0.189 |

[#]Median survival of control and ABA-treated mosquitoes from five lifespans in which mosquitoes received a weekly uninfected bloodmeal. Differences in lifespan between treatment groups were analyzed by log-rank test and Gehan-Breslow-Wilcoxon test.

Example 6: ABA Supplementation Reduces Parasitemia by Increasing *Plasmodium*-Specific IgG Production and Inflammasome Activation As described herein, oral supplementation with ABA decreased parasitemia in a mouse model of malaria and reduced transmission to mosquitoes. ABA had no direct effect on *Plasmodium falciparum* growth but enhanced the mammalian response to infection while also decreasing inflammatory pathology in the liver and spleen. In particular, ABA induced gene expression patterns indicative of inflammasome activation in the liver and antibody isotype switching in the spleen. Importantly, ABA-supplementation increased circulating levels of protective, parasite-specific IgG and required caspase-1 to reduce parasitemia.

FIG. 19A-C through FIG. 28A-B and Tables 6-1 through 6-4 support the use of ABA for treating *Plasmodium*-infected mammalian subjects. In the following tables, 4-5 mice were used per treatment, and data were analyzed by unpaired t-test. Tables 6-1 and 6-2 show that ABA supplementation had no effect on plasma indicators of organ health in uninfected and *P. yoelii*-infected mice. Tables 6-3 and 6-4 show that ABA supplementation had no effect on complete blood counts in uninfected and *P. yoelii*-infected mice.

Abbreviations for Tables 6-3 and 6-4 are as follows: WBC=white blood cells, RBCs=red blood cells, MCV=mean corpuscular volume, MCH=mean corpuscular hemoglobin, MCHC=mean corpuscular hemoglobin concentration, RDW=red blood cell distribution width, MPV=mean platelet volume.

TABLE 6-1

Small Animal Chemistry Panel of Uninfected Subjects

| | Control Mean | Control SE | ABA Mean | ABA SE | p value |
|---|---|---|---|---|---|
| albumin (g/dL) | 3.14 | 0.13 | 3.23 | 0.29 | 0.78 |
| alanine transaminase (U/L) | 363.7 | 225.2 | 176.8 | 61.06 | 0.5 |
| aspartate transaminase (U/L) | 1289 | 716.7 | 1437 | 536.3 | 0.88 |
| blood urea nitrogen (mg/dL) | 28 | 2.5 | 28.76 | 2.25 | 0.83 |
| creatine (mg/dL) | 0.17 | 0.01 | 0.21 | 0.03 | 0.13 |
| phosphorus (mg/dL) | 9.69 | 0.42 | 10.07 | 1.00 | 0.72 |
| total bilirubin (mg/dL) | 0.08 | 0.03 | 0.06 | 0.01 | 0.5 |
| total protein (g/dL) | 4.24 | 0.2 | 4.67 | 0.26 | 0.21 |

TABLE 6-2

Small Animal Chemistry Panel of *P. yoelii*-Infected Subjects

| | Py Mean | Py SE | Py + ABA Mean | Py + ABA SE | p value |
|---|---|---|---|---|---|
| albumin (g/dL) | 2.55 | 0.18 | 2.25 | 0.37 | 0.46 |
| alanine transaminase (U/L) | 34.74 | 5.18 | 30.23 | 1.22 | 0.47 |
| aspartate transaminase (U/L) | 137.5 | 14.3 | 194.7 | 42.88 | 0.21 |
| creatine (mg/dL) | 0.16 | 0.01 | 0.18 | 0.02 | 0.45 |
| phosphorus (mg/dL) | 8.61 | 0.42 | 8.43 | 0.31 | 0.75 |
| total bilirubin (mg/dL) | 0.25 | 0.03 | 0.26 | 0.04 | 0.82 |
| total protein (g/dL) | 4.41 | 0.2 | 4.12 | 0.41 | 0.51 |

TABLE 6-3

Complete Blood Counts of Uninfected Subjects

| | Control Mean | Control SE | ABA Mean | ABA SE | p value |
|---|---|---|---|---|---|
| WBC (K/uL) | 5.66 | 0.76 | 5.73 | 0.63 | 0.94 |
| % neutrophils | 15.35 | 2.01 | 17.53 | 3.97 | 0.64 |
| % lymphocytes | 69.89 | 3.2 | 66.56 | 3.94 | 0.53 |
| % monocytes | 10.28 | 0.89 | 11.71 | 0.94 | 0.3 |
| RBCs (M/ul) | 8.73 | 0.3 | 8.94 | 0.7 | 0.8 |
| hemoglobin (g/dL) | 11.7 | 0.52 | 12.56 | 0.86 | 0.42 |
| % hematocrit | 36.88 | 1.56 | 38.48 | 2.76 | 0.63 |
| MCV (fL) | 42.22 | 1.18 | 43.14 | 0.65 | 0.52 |
| MCH (g/dL) | 13.4 | 0.19 | 14.1 | 0.32 | 0.08 |
| MCHC (g/dL) | 31.76 | 0.87 | 32.72 | 0.75 | 0.43 |
| % RDW | 16.8 | 0.42 | 17.02 | 0.24 | 0.66 |
| platelets (K/ul) | 487.4 | 89.42 | 573.0 | 134.5 | 0.61 |
| MPV (fL) | 5.52 | 0.12 | 5.74 | 0.15 | 0.29 |

TABLE 6-4

Complete Blood Counts of *P. yoelii*-Infected Subjects[#]

| | Py Mean | Py SE | Py + ABA Mean | Py + ABA SE | p value |
|---|---|---|---|---|---|
| WBC (K/uL) | 31.27 | 0.29 | 31.90 | 3.63 | 0.89 |
| % neutrophils | 18.4 | 1.9 | 22.8 | 3.56 | 0.28 |
| % lymphocytes | 75.64 | 2.02 | 69.22 | 4.37 | 0.19 |
| % monocytes | 4.56 | 0.39 | 5.31 | 0.73 | 0.37 |

TABLE 6-4-continued

Complete Blood Counts of *P. yoelii*-Infected Subjects[#]

| | Py | | Py + ABA | | |
|---|---|---|---|---|---|
| | Mean | SE | Mean | SE | p value |
| RBCs (M/ul) | 3.97 | 0.26 | 3.83 | 0.31 | 0.72 |
| hemoglobin (g/dL) | 7.46 | 0.26 | 7.28 | 0.37 | 0.69 |
| % hematocrit | 22.02 | 0.97 | 21.00 | 1.36 | 0.55 |
| MCV (fL) | 55.76 | 1.55 | 55.20 | 1.57 | 0.81 |
| MCH (g/dL) | 18.92 | 0.59 | 19.18 | 0.67 | 0.78 |
| MCHC (g/dL) | 33.94 | 0.49 | 34.73 | 0.54 | 0.32 |
| % RDW | 37.14 | 0.99 | 34.95 | 2.07 | 0.34 |
| platelets (K/ul) | 278.0 | 14.8 | 234.3 | 23.48 | 0.14 |
| MPV (fL) | 6.46 | 0.07 | 6.23 | 0.11 | 0.11 |

We claim:

1. A method for treating malaria comprising: administering a composition comprising purified or synthetic abscisic acid, or a pharmaceutical salt thereof to a mammalian subject in need thereof under conditions effective for treating malaria.

2. The method of claim 1, wherein the subject is infected with *P. falciparum*, *P. vivax*, *P. ovale*, *P. malariae*, or *P. knowlesi*.

3. The method of claim 2, wherein treating malaria comprises alleviating a symptom of malaria experienced by the subject.

4. The method of claim 1, further comprising administering an effective amount of an additional antimalarial drug to the subject.

5. The method of claim 4, wherein the additional antimalarial drug comprises one or more compounds of the antimalarial classes selected from the group consisting of amino alcohols, aminoquinolines, antibiotics, antifolates, endoperoxides, and sulfonamides.

6. The method of claim 1, wherein the abscisic acid, or pharmaceutical salt thereof is administered to the subject at a dose of between 1 mg/kg/day and 1,000 mg/kg/day.

7. The method of claim 6, wherein the composition is administered orally or by injection.

8. A method for reducing *Plasmodium* parasitemia in a mammalian subject, comprising: administering a composition comprising purified or synthetic abscisic acid, or a pharmaceutical salt thereof to a mammalian subject in need thereof under conditions effective for reducing *Plasmodium* parasitemia in the subject.

9. The method of claim 8, wherein the conditions are further effective for reducing *Plasmodium* sp. gametocytemia in the subject.

10. A method for reducing transmission of *Plasmodium* by an *Anopheles* mosquito, comprising: administering a composition comprising purified or synthetic abscisic acid, or a pharmaceutical salt thereof to a mammalian subject infected with a *Plasmodium* under conditions effective for reducing transmission of the *Plasmodium* ingested by the mosquito in blood of the subject.

11. The method of claim 10, wherein the *Plasmodium* is a species selected from the group consisting of *P. falciparum*, *P. vivax*, *P. ovale*, *P. malariae*, and *P. knowlesi*.

12. The method of claim 5, wherein the additional antimalarial drug is an endoperoxide.

13. The method of claim 1, wherein the composition is administered orally.

14. The method of claim 8, wherein the composition is administered orally.

15. The method of claim 10, wherein the composition is administered orally.

16. The method of claim 12, wherein the endoperoxide is selected from the group consisting of artemether, arteether, artesunate, OZ439, OZ277, artemisinin, artemisone, and dihydroartemisinin.

17. The method of claim 12, wherein an additional antimalarial drug is not administered to the subject during treatment with the abscisic acid, or pharmaceutical salt thereof.

* * * * *